US010662159B2

(12) United States Patent
Makriyannis et al.

(10) Patent No.: US 10,662,159 B2
(45) Date of Patent: May 26, 2020

(54) ABHD6 AND DUAL ABHD6/MGL INHIBITORS AND THEIR USES

(71) Applicant: MAKScientific, LLC, Burlington, MA (US)

(72) Inventors: Alexandros Makriyannis, Watertown, MA (US); Michael Malamas, Jamison, PA (US); Manjunath Lamani, Medford, MA (US); Shrouq I. Farah, Everett, MA (US)

(73) Assignee: MAKSCIENTIFIC, LLC, Burlington, MA (US)

( * ) Notice: Subject to any disclaimer, the term of this patent is extended or adjusted under 35 U.S.C. 154(b) by 0 days.

(21) Appl. No.: 16/198,261

(22) Filed: Nov. 21, 2018

(65) Prior Publication Data

US 2019/0152917 A1 May 23, 2019

Related U.S. Application Data

(60) Provisional application No. 62/590,262, filed on Nov. 22, 2017.

(51) Int. Cl.
| | |
|---|---|
| *C07D 217/04* | (2006.01) |
| *C07D 209/44* | (2006.01) |
| *C07D 471/04* | (2006.01) |
| *C07D 223/16* | (2006.01) |
| *C07D 401/12* | (2006.01) |
| *C07D 205/12* | (2006.01) |
| *C07D 217/06* | (2006.01) |
| *C07D 413/12* | (2006.01) |
| *C07D 401/14* | (2006.01) |
| *C07D 403/12* | (2006.01) |

(52) U.S. Cl.
CPC ......... *C07D 217/04* (2013.01); *C07D 205/12* (2013.01); *C07D 209/44* (2013.01); *C07D 217/06* (2013.01); *C07D 223/16* (2013.01); *C07D 401/12* (2013.01); *C07D 401/14* (2013.01); *C07D 403/12* (2013.01); *C07D 413/12* (2013.01); *C07D 471/04* (2013.01)

(58) Field of Classification Search
CPC .. C07D 217/04; C07D 205/12; C07D 209/44; C07D 223/16; C07D 401/12; C07D 471/04
USPC .................................................. 514/210.18
See application file for complete search history.

(56) References Cited

U.S. PATENT DOCUMENTS

2018/0208607 A1* 7/2018 Brodney .............. C07D 221/20
2018/0208608 A1* 7/2018 Brodney ................... A61P 3/00

FOREIGN PATENT DOCUMENTS

WO     WO 2009/117444 A1     9/2009

OTHER PUBLICATIONS

Abadji, et al., "Involvement of the Carboxyl Terminus of the Third Intracellular Loop of the Cannabinoid CB 1 Receptor in Constitutive Activation of G,", *J. Neur.* 1999, 2 2032-2038.
Alapafuja et al., "Sulfonyl Fluoride Inhibitors of Fatty Acid Amide Hydrolase", *J. Med. Chem.* (2012) 55: 10074-10089.
Bonz, et. al., "Cannabinoids Acting on $CB_1$ Receptors Decrease Contractile Performance in Human Atrial Muscle", *J. Cardiovasc. Pharmacol.* 2003, 41, 657-664.
Cota, et al., "The endogenous cannabinoid system affects energy balance via central orexigenic drive and peripheral lipogenesis", *J. Clin. Invest.* Aug. 2003, 112(3): 423-431.
Dinh, et al., "Brain monoglyceride lipase participating in endocannabinoid inactivation", *Proceedings of the National Academy of Science of the United States of America*, Aug. 6, 2002, 99(16): 10819-10824.
Dodd, et al,. "A Rapid Method for Preparing Synaptosomes: Comparison with Alternative Procedures", *Brain Res.* (1981), 226, 107-118.
Egertová, et al., "Localisation of Cannabinoid Receptors in the Rat Brain Using Antibodies to the Intracellular C-Terminal Tail of CB1", *J. Comp. Neurol.* 2000, 422,159-171.
Engeli, et. al., "Activation of the Peripheral Endocannabinoid System in Human Obesity", *Diabetes* 2005, 54(10), 2838-2843.
Gong, et. al., "Cannabinoid CB2 receptors: Immunohistochemical localization in rat brain" *Brain Res.* 2006, 1071, 10-23.
Guo, et. al. "(−)-11-Hydroxy-7'-isothiocyanato-1',1'-dimethylheptyl-$\Delta^8$-THC: A Novel, High-Affinity Irreversible Probe for the Cannabinoid Receptor in the Brain" *J. Med. Chem.* 1994, 37, 3867-3870.
Herkenham, et al., "Characterization and Localization of Cannabinoid Receptors in Rat Brain: A Quantitative in vitro Autoradiographic Study", *J. Neurosci.* 1991,11(2), 563-583.
Howlett, et al. "International Union of Pharmacology. XXVII. Classification of Cannabinoid Receiptors", *Pharmacol. Rev.* 2002, 54(2): 161-202.
Karlson et al., "cDNA Cloning, Tissue Distribution, and Identification of the Catalytic Triad of Monoglyceride Lipase", *Biol. Chem.*, Oct. 24, 1997, 272 (43): 27218-27223.
Lan et. al., "Structure-Activity Relationships of Pyrazole Derivatives as Cannabinoid Receptor Antagonists", *J. Med. Chem.* 1999, 42, 769-776.
Mallat, et al., "Endocannabinoids and Liver Disease. I. Endocannabinoids and their receptors in the liver", *Am. J. Physiol. Gastrointest. Liver Physiol.*, 2008, 294, G9-G12.

(Continued)

*Primary Examiner* — Kristin A Vajda
(74) *Attorney, Agent, or Firm* — Hamilton, Brook, Smith & Reynolds, P.C.

(57) ABSTRACT

Provided herein are compounds and pharmaceutical compositions for selectively inhibiting serine hydrolase a/b-hydrolase domain 6 (ABHD6) and dually inhibiting ABHD6 and monoacylglycerol lipase (MGL). The compounds and pharmaceutical compositions disclosed herein are useful for treating a number of therapeutic conditions related to cannabinergic receptor function such as pain, inflammation, neuropathy, neurodegenerative diseases, anxiety disorders, motor function disorder, metabolic disorder, glaucoma and chemotherapy-induced nausea and vomiting and cancer.

8 Claims, No Drawings

(56) References Cited

OTHER PUBLICATIONS

Mans, et al, "The serine hydrolase ABHD6 controls the accumulation and efficacy of 2-AG at cannabinoid receptors", *Nat. Neurosci.* 13(8): 951-957, Aug. 2010.
Morse, et al. "A Novel Electrophilic High Affinity Irreversible Probe for the Cannabinoid Receptor", *Life Sci.* 1995, 56, 1957-1962.
Mukhopadhyay, et al., "Pharmacological Inhibition of $CB_1$ Cannabinoid Receptor Protects Against Doxorubicin-Induced Cardiotoxicity", *J. Am. Coll. Cardiol.* 2007, 50(6): 528-536.
Naydenov, et al., "ABHD6 Blockade Exerts Antiepileptic Activity in PTZ-Induced Seizures and in Spontaneous Seizures in R6/2 Mice", *Neuron.*, Jul. 16, 2014 83(2), 361-371.
Pacher, et al., The Endocannabinoid System as an Emerging Target of Pharmacotherapy, *Pharmacol. Rev.* Sep. 2006, 58(3): 389-462.
Patricelli, et al. "Comparative Characterization of a Wild Type and Transmembrane Domain-Deleted Fatty Acid Amide Hydrolase: Identification of the Transmembrane Domain as a Site for Oligomerization", *Biochemistry* (1998) 37: 15177-15187.
Rajesh, et al., "$CB_2$ cannabinoid receptor agaonists attenuate TNF-α-induced human vascular smooth muscle cell proliferation and migration", *Br. J. Pharmacol.* 2008, 153, 347-357.
Rajesh, et. al., "$CB_2$-receptor stimulation attenuates TNF-α-induced human endothelial cell activation, transendothelial migration of monocytes, and monocyte-endothelial adhesion", *Am. J. Physiol. Heart. Circ. Physiol.* 2007, 293(4), 2210-2218.
Savinainen, et al., "The serine hydrolases MAGL, ABHD6 and ABHD12 as guardians of 2-arachidonoylglycerol signaling through cannabinoid receptors", *Acta Physiol.* 2012, 204, 267-276.
Schlosburg, et al., "Chronic monoacylglycerol lipase blockade causes functional antagonism of the endocannabinoid system", *Nature Neuroscience*, Sep. 2010, 13(9): 1113-1119.
Tchantchou, et al., "Selective Inhibition of Alpha/Beta-Hydrolase Domain 6 Attenuates Neurodegeneration, Alleviates Blood Brain Barrier Breakdown, and Improves Functional Recovery in a Mouse Model of Traumatic Brain Injury", *Journal of Neurotrauma*, Apr. 1, 2013, 30:565-579.
Thomas et al., "The Serine Hydrolase ABHD6 is a Critical Regulator of the Metabolic Syndrome", *Cell Reports* 2013, 5, 508-520.
Van Sickle, et al., "Neuroscience: Identification and Functional Characterization of Brainstem Cannabinoid CB2 Receptors", *Science*, Oct. 14, 2005, 310, 329-332.
Zhao et al., "α/β-Hydrolase domain-6 and saturated long chain monoacylglycerol regulate insulin secretion promoted by both fuel and non-fuel stimuli", Molecular Metabolism 2015, 4, 940-950.
Zvonok, et al., "Full Mass Spectrometric Characterization of Human Monoacylglycerol Lipase Generated by Large-Scale Expression and Single-Step Purification", *J. Proteome Res.* (May 2008) 7(5): 2158-2164.
Zvonok et al. "Covalent Inhibitors of Human Monoacylglycerol Lipase: Ligand-assisted Characterization of the Catalytic Site by Mass Spectrometry and Mutational Analysis", Chem. Biol. (2008) 15(8): 854-862.

* cited by examiner

ABHD6 AND DUAL ABHD6/MGL INHIBITORS AND THEIR USES

RELATED APPLICATION

This application claims the benefit of U.S. Provisional Application No. 62/590,262, filed on Nov. 22, 2017. The entire teachings of the above application are incorporated herein by reference.

GOVERNMENT SUPPORT

This invention was made with government support under R01DA003801 from the National Institutes of Health. The government has certain rights in the invention.

BACKGROUND

Cannabinoid receptors, CB1 and CB2, are part of the endocannabinoid system (ECS), which consists of cannabinoid receptors, endogenous endocannabinoids anandamide (AEA) and 2-arachindonoylglycerol (2-AG) and the hydrolytic enzymes fatty acid amide hydrolase (FAAH) and monoacylglycerol lipase (MGL), a/b-hydrolase domain 6 (ABHD6) and a/b-hydrolase domain 12 (ABHD12) which are responsible for hydrolyzing AEA and 2-AG. FAAH is the principal enzyme for the in vivo degradation of AEA, while MGL, ABHD6 and ABHD12 together account for approximately 99% of 2-AG hydrolase activity. MGL colocalizes with CB1R in axon terminals and is responsible for approximately 85% of 2-AG hydrolysis (Savinainen, et. al., Acta Physiol. 2012, 204, 267-276). ABHD6 resides post-synaptically, often juxtaposed with CB1Rs, and its inhibition leads to activity-dependent accumulation of 2-AG. MGL and ABHD6 possess distinct sub-cellular locations in neurons which result in independent control of 2-AG accumulation and contribute to the fine-tuning of the magnitude and duration of the 2-AG signaling for the cannabinoid receptors. Specifically, when measuring 2-AG hydrolysis in neuron homogenates, ABHD6 and MAGL contribute about equally (Marrs et al., Nat. Neurosci. 13, 951-957, 2010).

The magnitude and duration of the in vivo CB1 and/or CB2 receptor modulation by 2-AG is relatively short, presumably due to its rapid inactivation process involving deactivating enzymes MGL (Karlson et. al., Biol. Chem. 1997, 272, 27218-27223) and ABHD6 (Marrs et al., Nat. Neurosci. 13, 951-957, 2010). MGL is a cytosolic enzyme that is also known for its ability to hydrolyze several bioactive fatty acid glyceryl esters not belonging to the endocannabinoid family, for example, 2-oleolglycerol and 2-palmitoyl glycerol. MGL plays dual roles in physiologic processes by regulating endocannabinoid tone as well as lipogenesis (Dinh, et. al., *Proceedings of the National Academy of Science of the United States of America* 2002, 99, 10819; Schlosburg et. al., *Nature Neuroscience* 2010, 13, 1113. ABHD6 is an integral membrane enzyme and a rate-limiting step of 2-AG signaling. Therefore, ABHD6 represents a useful target for modulation of cannabinoid receptors dependent disorders, alone or in conjunction with MGL.

Both cannabinoid receptors CB1 and CB2 belong to the GPCR family and have very different functions and distributions. The CB1 receptor is abundantly expressed in the central nervous system (CNS) and at lower levels in various peripheral tissues, including vascular and endothelial and smooth muscle cells, liver, skeletal muscle and adipose tissues (Herkenham, et. al., *J. Neurosci.* 1991, 11, 563-83; Egertova, et. al., *J. Comp. Neurol.* 2000, 422, 159-71; Bonz, et. al., *J. Cardiovasc. Pharmacol.* 2005, 41, 657-664; Mallat, et. al., *Am. J. Physiol. Gastrointest. Liver Physiol.* 2008, 294, 9-12; Pacher, et. al., *Pharmacol. Rev.* 2006, 58, 389-462; Howlett, et. al. *Pharmacol. Rev.* 2002, 54, 161-202; Mukhopadhyay, et. al., *J. Am. Coll. Cardiol.* 2007, 50, 528-536; Engeli, et. al., *Diabetes* 2005, 54, 2938-2843; Cota, et. al., *J. Clin. Invest.* 2003, 112, 423-431).

The CB2 receptor is mainly expressed in immune and hematopoietic cells and recently was also identified in the liver, and human coronary endothelium and smooth muscle cells, and at a lower level than CB1 in the brain. (Mukhopadhyay, et. al., *J. Am. Coll. Cardiol.* 2007, 50, 528-536; Mallat, et. al., *Am. J. Physiol. Gastrointest. Liver Physiol.* 2008, 294, 9-12; Rajesh, et. al., *Br. J. Pharmacol.* 2008, 153, 347-357; Van Sickle, et. al., *Science,* 2005, 310, 329-332; Gong, et. al., Brain Res. 2006, 1071, 10-23; Rajesh, et. al., *Am. J. Physiol. Heart. Circ. Physiol.* 2008, 293, 2210-22180.

The cannabinoid receptors CB1 and CB2 are involved in a variety of physiological or pathophysiological processes in humans and animals, e.g., processes related to the central nervous system, immune system, cardiovascular system, endocrine system, respiratory system, the gastrointestinal tract or to reproduction. Therefore, compounds which endogenously increase 2-AG levels are suitable for modulating these receptors and are useful in the prevention and/or treatment of cannabinoid receptor-related disorders. Conditions that may treated by modulation of the cannabinoid receptors include, for example, pain, neuropathic pain, neurodegenerative diseases including Alzheimer's disease, Parkinson's disease, amyotrophic lateral sclerosis, mental disorders such as schizophrenia and depression, gastrointestinal motility disorders such as irritable bowel syndrome, coronary arteries disease, eating disorders such as anorexia nervosa and bulimia, also metabolic diseases such as obesity, diabetes, liver steatosis, metabolic syndrome, various inflammatory conditions and ocular diseases as well as other illness in which the cannabinoid system is implicated.

Naturally occurring cannabinoids as well as their synthetic analogues are employed for the modulation of the functional response of the cannabinoid receptors which translates to a physiological effect. The most widely used natural cannabinoid $\nabla^9$-tetrahydrocannabinol ($\nabla^9$-THC), is the major bioactive constituent of *Cannabis sativa* (marihuana). Compounds can bind to the CB1 and/or CB2 in an individual or animal. There are well-established in vitro methods to assay the ability of a compound to bind to CB1 and/or CB2 receptors, as well as cell-based assays to study the functional response of the compound upon binding with the CB1 and/or the CB2 receptors (Abadji, et. al., *J. Neur.* 1999, 2 2032-20388; Dodd, et. al. Brain Res. 1981, 226, 107-18; Guo, et. al. *J. Med. Chem.* 1994, 37, 3867-3880; Morse, et. al. *Life Sci.* 1995, 56, 1957-1962, Lan et. al., *J. Med. Chem.* 1999, 42, 769-776).

The serine hydrolases ABHD6 and MGL hydrolyze the most abundant endocannabinoid (eCB) in the brain 2-arachidonoylglycerol (2-AG) and control its availability at cannabinoid receptors. In neurons, ABHD6 is located in postsynaptic dendrites at the site of 2-AG synthesis, where it fine-tunes the stimulated production of 2-AG and the resulting activation of presynaptic CB1 cannabinoid receptors (Marrs et al., *Nat. Neurosci.* 13, 951-957, 2010). MGL is localized in presynaptic axon terminals. Therefore, inhibitors of ABHD6 and/or ABHD6/MGL will independently control 2-AG accumulation and contribute to the fine-tuning of the magnitude and duration of the 2-AG signaling for the cannabinoid receptors and are useful in the prevention and/or treatment of cannabinoid-receptor related disorders. Recent studies suggested that ABHD6 inhibitors hold promise as therapeutics for obesity, nonalcoholic fatty liver disease, type II diabetes (Gwynneth et al., Cell Reports 2013, 5, 508-520) and insulin secretion regulation (Zhao et al., Molecular Metabolism 2015, 4, 940e950), traumatic brain injury (TBI) (Tchantchou et al., Journal Of Neurotrauma 2013, 30:565-579) and epilepsy (Naydenov et al., Neuron. 2014 16 83(2), 361-371).

The medicinal chemistry landscape of selective ABHD6 inhibitors and dual acting ABHD6/MGL inhibitors as pharmacological probes aimed at modulating 2-AG levels is limited.

SUMMARY

The present invention provides compounds and pharmaceutical compositions for selectively inhibiting serine hydrolase a/b-hydrolase domain 6 (ABHD6) and also dually inhibiting ABHD6 and monoacylglycerol lipase (MGL). Both enzymes ABHD6 and MGL hydrolyze the endocannabinoid 2-arachidonoylglycerol (2-AG) which regulates neurotransmission and neuroinflammation by activating CB1 cannabinoid receptors on neurons and CB2 cannabinoid receptors on microglia. Modulation of the endocannabinoid system is known to offer numerous pharmacological benefits. The disclosed compounds when administered in a therapeutically effective dose to an individual or animal translate to a physiological response of the cannabinergic receptor though augmentation of 2-AG levels. The physiological response may be useful to treat a number of therapeutic conditions related to cannabinergic receptor function such as, but not limited to pain, inflammation, neuropathy, neurodegenerative diseases, anxiety disorders, motor function disorder, metabolic disorder, glaucoma and chemotherapy induced nausea and vomiting and cancer. The present invention also provides methods for preparing these compounds.

In one embodiment, the compounds are represented by Formula I or Formula II:

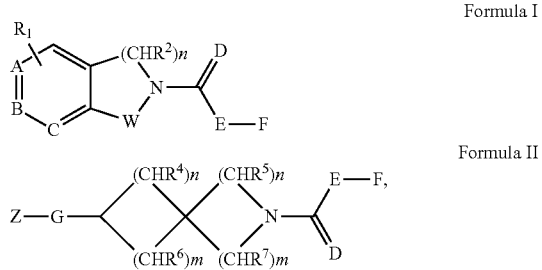

or a stereoisomer thereof, or a pharmaceutically acceptable salt of either of the foregoing, wherein variables A, B, C, D, E, F, G, W, Z, $R^1$, $R^2$, $R^4$, $R^5$, $R^6$, $R^7$, n and m are as defined anywhere herein.

The present invention further provides methods of preparing compounds described herein.

The present invention further provides pharmaceutical compositions comprising one or more of the compounds of the invention, or a stereoisomer thereof, or a pharmaceutically acceptable salt of the foregoing and a pharmaceutically acceptable carrier.

The present invention further comprising a method of treating a cannabinoid receptor-mediated disease or disorder in a patient in need thereof, comprising administering to the patient a therapeutically effective amount of a compound of the invention, or a stereoisomer thereof, or a pharmaceutically acceptable salt of the foregoing. The present invention further provides a compound for use in treating a cannabinoid receptor-mediated disease or disorder, wherein the compound is a compound of the invention, a stereoisomer thereof, or a pharmaceutically acceptable salt of the foregoing. The present invention further provides use of compounds of the invention, or a stereoisomer thereof, or a pharmaceutically acceptable salt of the foregoing, for the manufacture of a medicament for treating a cannabinoid receptor-mediated disease or disorder. Cannabinoid receptor-mediated diseases and disorders include, but are not limited to, Type-2 diabetes; liver steatosis; ocular disease such as glaucoma, uveitis, retina inflammation, retina degeneration pain; neuropathic pain; neurodegenerative diseases including Alzheimer's disease, Parkinson's disease, amyotrophic lateral sclerosis; spinal cord injury; mental disorders such schizophrenia and depression; gastrointestinal motility disorders such as irritable bowel syndrome; coronary arteries disease; ocular hypertension; eating disorders such as anorexia nervosa and bulimia, as well as other illness in which the cannabinoid system is implicated.

The details of one or more embodiments of the invention are set forth in the accompa-nying description below. Other features, objects, and advantages of the invention will be apparent from the description, and from the claims.

DETAILED DESCRIPTION

A description of example embodiments follows.

The present invention relates to the discovery of ABHD6 inhibitors and dual ABHD6/MGL inhibitors and methods suitable for the treatment of various diseases associated with modulation of the cannabinoid receptors through elevation of 2-AG levels in a cell, organ, or even the entire body. Most preferably, such modulation will result in treatment and/or prevention of Type-2 diabetes; liver steatosis; ocular disease such as glaucoma, uveitis, retina inflammation, retina degeneration pain; neuropathic pain; neurodegenerative diseases including Alzheimer's disease, Parkinson's disease, amyotrophic lateral sclerosis; spinal cord injury; mental disorders such schizophrenia and depression; gastrointestinal motility disorders such as irritable bowel syndrome; coronary arteries disease; ocular hypertension; eating disorders such as anorexia nervosa and bulimia, as well as other illness in which the cannabinoid system is implicated.

For example, it has now been found that bicyclic compounds of formula I (e.g., isoquinoline, isoindoline), and related spiro-analogs of formula II demonstrate inhibition of ABHD6 and/or MGL. Advantageously, compounds of formula I and/or II may be used as effective therapeutic agents for the treatment, prevention or amelioration of a disease or disorder characterized by pain and inflammation manifestations in a patient.

Compounds

This invention relates to compounds of formula I and formula II and to pharmaceutically acceptable salts, solvates and derivatives, such as pro-drugs and metabolites, thereof. This invention also related to compound of formula I and formula II, or a stereoisomer thereof, or a pharmaceutically acceptable salt of the foregoing. Compounds of formula I and II are represented by the following structural formulas, respectively:

Formula I

Formula II

A first embodiment is a compound of formula I, or a stereoisomer thereof, or a pharmaceutically acceptable salt of the foregoing, wherein:

A, B and C are independently selected from —C(H)— or nitrogen;

W=(CHR$^3$)m or none, when W is none, the nitrogen is directly attached to the aromatic ring;

D=O or S;

E=O, NH, or none, when E is none, F is directly attached to C=D;

F is selected from n and m are each independently 1, 2, 3 or 4; and

R$^1$ is selected from H; halogen; C$_1$-C$_{10}$alkyl; C$_1$-C$_{10}$alkyl-oxy; C$_3$-C$_8$cycloalkyl; C$_3$-C$_8$cycloalkyl-oxy; C$_1$-C$_{10}$alkyl or C$_1$-C$_{10}$alkyl-oxy substituted at the terminal carbon with halogen, haloalkyl, haloalkoxy, alkoxy, alkenyl, alkynyl, NR$^8$R$^9$, CN, ONO$_2$, aryl, O-aryl, O-aralkyl, NR$^{10}$-aryl, NR$^{11}$-aralkyl, O-heteroaryl, NR$^{12}$-heteroaryl, or saturated or unsaturated four-, five-, six- or seven-membered ring which can contain up to 3 heteroatoms selected from N, N-oxide, S and O; or saturated or unsaturated four-, five-, six- or seven-membered ring which can contain up to 3 heteroatoms selected from N, N-oxide, S and O; or $$R^1 = L-\overset{(CH_2)n'}{\underset{(CH_2)m'}{N}}-K-$$

wherein:

K=—(CH$_2$)n, —O(CH$_2$)n-, —(CH$_2$O)n-, —(CH$_2$)nNR$^8$—, —O(CH$_2$)nO— or none, when K is none, the nitrogen is directly attached to the aromatic ring;

n' and m' are each independently 1, 2, 3 or 4;

L=CH$_2$, O, S, SO, SO$_2$, CO, NH, or NR$^{14}$;

R$^2$ and R$^3$ are each independently H, C$_1$-C$_5$ alkyl, aryl, or heteroaryl; and R$^8$, R$^9$, R$^{10}$, R$^{11}$, R$^{12}$, and R$^{14}$ are each independently H, C$_1$-C$_5$alkyl, or C$_3$-C$_8$cycloalkyl.

In a first aspect of the first embodiment:

W=(CHR$^3$)m;

D=O;

E=O or NH;

n and m are each independently 1 or 2;

R$^1$ is selected from H; halogen; C$_1$-C$_5$alkyl; C$_1$-C$_5$alkyl-oxy; C$_3$-C$_6$cycloalkyl; C$_3$-C$_6$cycloalkyl-oxy; C$_1$-C$_5$alkyl or C$_1$-C$_5$alkyl-oxy substituted at the terminal carbon with halogen, haloalkyl, haloalkoxy, alkoxy, alkenyl, alkynyl, NR$^8$R$^9$, CN, ONO$_2$, aryl, O-aryl, O-aralkyl, NR$^{10}$-aryl, NR$^{11}$-aralkyl, O-heteroaryl, NR$^{12}$-heteroaryl, or saturated or unsaturated four-, five-, six- or seven-membered ring which can contain up to 3 heteroatoms selected from N, N-oxide, S and O; or saturated or unsaturated four-, five-, six- or seven-membered ring which can contain up to 3 heteroatoms selected from N, N-oxide, S and O; or

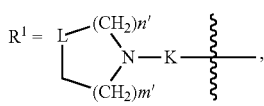

wherein:

K=—(CH$_2$)n, —O(CH$_2$)n-, —(CH$_2$O)n-, —(CH$_2$)nNR$^8$—, —O(CH$_2$)nO- or none, when K is none, the nitrogen is directly attached to the aromatic ring;

n' and m' are each independently 1, 2 or 3;

L=CH$_2$, O, S, SO, SO$_2$, CO, NH or NR$^{14}$;

R$^2$ and R$^3$ are each independently H, C$_1$-C$_5$ alkyl, aryl, or heteroaryl; and R$^8$, R$^9$, R$^{10}$, R$^{11}$, R$^{12}$, and R$^{14}$ are each independently H, C$_1$-C$_3$alkyl, or C$_3$-C$_5$cycloalkyl.

Values for the remaining variables are as described anywhere herein (e.g., in the first embodiment).

In a second aspect of the first embodiment, E=O. Values for the remaining variables are as described anywhere herein (e.g., in the first embodiment, or first aspect thereof).

In a third aspect of the first embodiment, F is

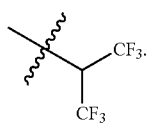

Values for the remaining variable are as described anywhere herein (e.g., in the first embodiment, or first or second aspect thereof).

In a fourth aspect of the first embodiment, R$^1$ is selected from H; C$_1$-C$_{10}$alkyl; C$_1$-C$_{10}$alkyl-oxy; C$_3$-C$_8$cycloalkyl; C$_3$-C$_8$cycloalkyl-oxy; C$_1$-C$_{10}$alkyl or C$_1$-C$_{10}$alkyl-oxy substituted at the terminal carbon with halogen, haloalkyl, haloalkoxy, alkoxy, alkenyl, alkynyl, NR$^8$R$^9$, CN, ONO$_2$, aryl, O-aryl, O-aralkyl, NR$^{10}$-aryl, NR$^{11}$-aralkyl, O-heteroaryl, NR$^{12}$-heteroaryl, or saturated or unsaturated four-, five-, six- or seven-membered ring which can contain up to 3 heteroatoms selected from N, N-oxide, S and O; or saturated or unsaturated four-, five-, six- or seven-membered ring which can contain up to 3 heteroatoms selected from N, N-oxide, S and O; or

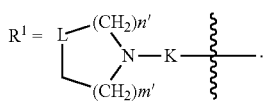

Values for the remaining variables are as described anywhere herein (e.g., in the first embodiment, or first through third aspects thereof).

A second embodiment, is a compound of formula II, or a stereoisomer thereof, or a pharmaceutically acceptable salt of the foregoing, wherein:

D=O or S;

E=O, NH, or none, when E is none, F is directly attached to C=D;

F is selected from

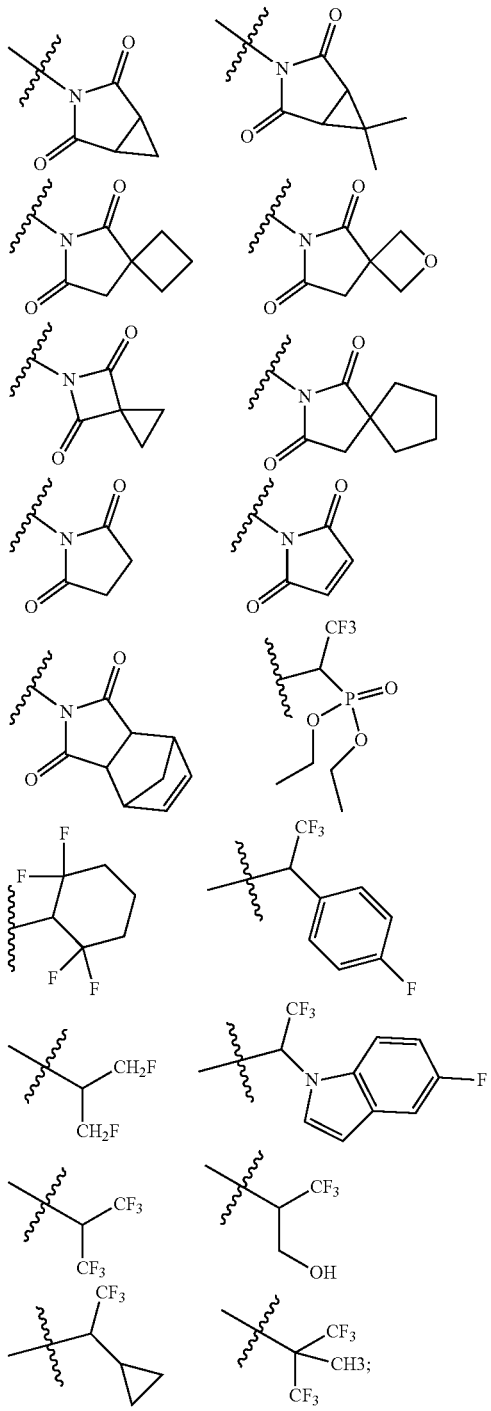

each n and each m are independently 1, 2 or 3;

G=O, NH, NR$^{13}$, or none, when G is none, G is directly attached to the cyclic ring;

Z is selected from H; halogen; C$_1$-C$_{10}$alkyl; C$_1$-C$_{10}$alkyl-oxy; C$_3$-C$_8$cycloalkyl; C$_3$-C$_8$cycloalkyl-oxy; C$_1$-C$_{10}$alkyl or C$_1$-C$_{10}$alkyl-oxy substituted at the terminal carbon with halogen, haloalkyl, haloalkoxy, alkoxy, alkenyl, alkynyl, NR$^8$R$^9$, CN, ONO$_2$, aryl, O-aryl, O-aralkyl, NR$^{10}$-aryl, NR$^{11}$-aralkyl, O-heteroaryl, NR$^{12}$-heteroaryl, or saturated or unsaturated four-, five-, six- or seven-membered ring which can contain up to 3 heteroatoms selected from N, N-oxide, S and O; or saturated or unsaturated four-, five-, six- or seven-membered ring which can contain up to 3 heteroatoms selected from N, N-oxide, S and O;

$R^4$, $R^5$, $R^6$, and $R^7$ are each independently H or $C_1$-$C_3$ alkyl; and $R^8$, $R^9$, $R^{10}$, $R^{11}$, $R^{12}$, and $R^{13}$ are each independently H, $C_1$-$C_5$alkyl, or $C_3$-$C_8$cycloalkyl.

In a first aspect of the second embodiment, E=O or NH; and each n and each m are independently 1, 2 or 3. Values for the remaining variables are as described anywhere herein (e.g., in the second embodiment).

In a second aspect of the second embodiment, E=O. Values for the remaining variables are as described anywhere herein (e.g., in the second embodiment, or first aspect thereof).

In a third aspect of the second embodiment, F is

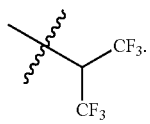

Values for the remaining variable are as described anywhere herein (e.g., in the second embodiment, or first or second aspect thereof).

In a fourth aspect of the second embodiment, Z is selected from H; $C_1$-$C_{10}$alkyl; $C_1$-$C_{10}$alkyl-oxy; $C_3$-$C_8$cycloalkyl; $C_3$-$C_8$cycloalkyl-oxy; $C_1$-$C_{10}$alkyl or $C_1$-$C_{10}$alkyl-oxy substituted at the terminal carbon with halogen, haloalkyl, haloalkoxy, alkoxy, alkenyl, alkynyl, $NR^8R^9$, CN, $ONO_2$, aryl, O-aryl, O-aralkyl, $NR^{10}$-aryl, $NR^{11}$-aralkyl, O-heteroaryl, $NR^{12}$-heteroaryl, or saturated or unsaturated four-, five-, six- or seven-membered ring which can contain up to 3 heteroatoms selected from N, N-oxide, S and O; or saturated or unsaturated four-, five-, six- or seven-membered ring which can contain up to 3 heteroatoms selected from N, N-oxide, S and O; or

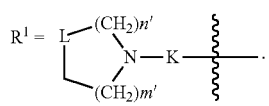

Values for the remaining variables are as described anywhere herein (e.g., in the second embodiment, or first through third aspects thereof).

One embodiment is a compound of formula I or II, wherein:

A, B and C are selected individually, in pairs, or together from carbon or nitrogen;

W=$(CHR^3)m$ or none, when W is none the nitrogen is directly attached to the aromatic ring;

D=O, S;

E=O, NH, or none, when E is none F is directly attached to C=D;

F is selected from

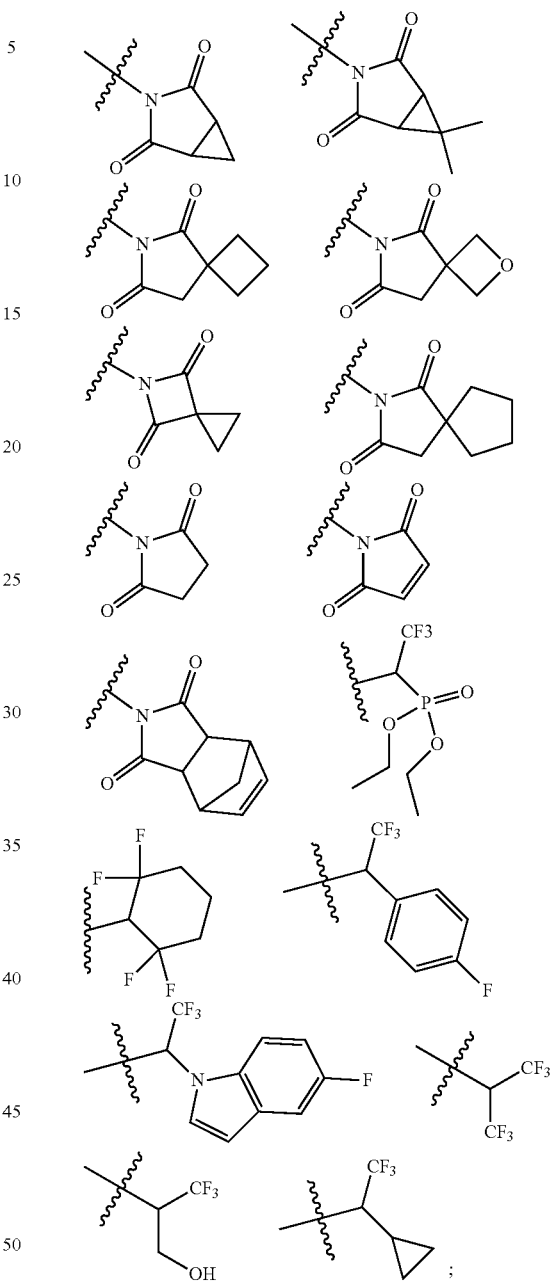

G=O, NH, $NR^{13}$, or none, when G is none Z is directly attached to the cyclic ring;

n, m=1-4;

$R^1$ is selected from H, $C_1$-$C_{10}$alkyl group straight-chain or branched, $C_1$-$C_{10}$alkyl-oxy, $C_3$-$C_8$cycloalkyl, $C_3$-$C_8$cycloalkyl-oxy, $C_1$-$C_{10}$alkyl or $C_1$-$C_{10}$alkyl-oxy substituted at the terminal carbon with halogen, haloalkyl, haloalkoxy, alkoxy, alkenyl, alkynyl, $NR^8R^9$, CN, $ONO_2$, aryl, O-aryl, O-aralkyl, $NR^{10}$-aryl, $NR^{11}$-aralkyl, O-heteroaryl, $NR^{12}$-heteroaryl, saturated or unsaturated four-, five-, six- or seven-membered ring which can contain up to 3 heteroatoms selected from N, N-oxide, S and O; saturated or unsaturated four-, five-, six- or seven-membered ring which can contain up to 3 heteroatoms selected from N, N-oxide, S and O;

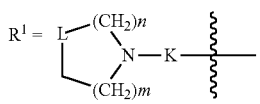

wherein

K=—(CH$_2$)n, —O(CH$_2$)n-, —(CH$_2$O)n, or none, when K is none the nitrogen is directly attached to the aromatic ring;

n, m=1-4;

L=CH$_2$, O, S, SO, SO$_2$, CO, NH, NR$^{14}$;

R$^2$, R$^3$ can be independently H, C$_1$-C$_5$ alkyl group straight-chain or branched, aryl, heteroaryl;

Z is selected from aryl, heteroaryl, aralkyl, heteroalkyl, C$_1$-C$_{10}$alkyl group straight-chain or branched, C$_1$-C$_{10}$alkyl-oxy, C$_3$-C$_8$cycloalkyl, C$_3$-C$_8$cycloalkyl-oxy, C$_1$-C$_{10}$alkyl or C$_1$-C$_{10}$alkyl-oxy substituted at the terminal carbon with halogen, haloalkyl, haloalkoxy, alkoxy, alkenyl, alkynyl, NR$^8$R$^9$, CN, ONO$_2$, aryl, O-aryl, O-aralkyl, NR$^{10}$-aryl, NR$^{11}$-aralkyl, O-heteroaryl, NR$^{12}$-heteroaryl, saturated or unsaturated four-, five-, six- or seven-membered ring which can contain up to 3 heteroatoms selected from N, N-oxide, S and O; saturated or unsaturated four-, five-, six- or seven-membered ring which can contain up to 3 heteroatoms selected from N, N-oxide, S and O;

R$^4$, R$^5$, R$^6$, R$^7$ can be independently H, C$_1$-C$_3$ alkyl;

R$^8$, R$^9$, R$^{10}$, R$^{11}$, R$^{12}$, R$^{13}$, R$^{14}$ can be independently H, C$_1$-C$_5$alkyl group straight-chain, branched, or C$_3$-C$_8$cycloalkyl;

a stereoisomer thereof; or a pharmaceutically acceptable salt thereof.

It is understood that the claims encompass all possible stereoisomers and pro-drugs.

The term "aryl", as used herein, refers to an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. The term "aryl" further includes both unsubstituted carbocylic groups and carbocylic groups containing 1-5-substitutions.

The term "heteroaryl" as used herein means an aromatic heterocyclic ring system, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quaternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, α-carboline, or the like.

When the terms aryl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 6, more preferably up to 4 carbon atoms.

Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both (C1-C10) straight chain and (C3-C12) branched-chain (unless defined otherwise) monovalent saturated hydrocarbon moieties. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. "Lower alkyl" refers to (C1-C5) straight chain and (C3-C5) branched chain alkyl groups. Specifically included within the definition of "alkyl" are those alkyl groups that are optionally substituted. Suitable alkyl substitutions include, but are not limited to, CN, OH, halogen, phenyl, carbamoyl, carbonyl, alkoxy or aryloxy.

The term "hydroxyl group" is represented by the formula —OH. The term "alkoxy group" or "alkyloxy" is represented by the formula —OR, where R can be an alkyl group, optionally substituted with an alkenyl, alkynyl, aryl, aralkyl, cycloalkyl, halogenated alkyl, or heterocycloalkyl group as described above.

The term "cycloalkyloxy" is represented by the formula —OR, where R is a cycloalkyl group, as described herein.

The term "hydroxyalkyl group" refers to an alkyl group that has at least one hydrogen atom substituted with a hydroxyl group. The term "alkoxyalkyl group" is defined as an alkyl group that has at least one hydrogen atom substituted with an alkoxy group described above. Where applicable, the alkyl portion of a hydroxyalkyl group or an alkoxyalkyl group can have, for example, aryl, aralkyl, halogen, hydroxy and/or alkoxy substituents.

The term "amine group" is represented by the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

The term "aralkyl" refers to an aryl group having an alkyl group, as defined above, attached to the aryl group. Examples of aralkyl groups include, without limitation, benzyl groups and trityl groups.

As used in the specification, the term "halogen" designates F, Cl, Br or I and the term "haloalkyl" as used herein designates a CnH2n+1 group having from one to 2n+1 halogen atoms which may be the same or different and the term haloalkoxy as used herein designates an $OC_nH_{2n+1}$ group having from one to 2n+1 halogen atoms which may be the same or different. Preferably the term haloalkyl designates $CF_3$ and the term haloalkoxy designates $OCF_3$, $OCHF_2$. Examples of haloalkyl groups include CF3, CH2Cl, C2H3BrCl, C3H5F2, or the like.

"Haloalkoxy," as used herein, refers to —OR, wherein R is a haloalkyl group described herein.

The term "alkenyl", as used herein, refers to either a (C2-C8) straight chain or (C3-C10) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, and the like.

The term "alkynyl", as used herein, refers to either a (C2-C8) straight chain or (C3-C10) branched-chain monovalent hydrocarbon moiety containing at least one triple bond. Such hydrocarbon alkynyl moieties may be mono or polyunsaturated. Examples of mono or polyunsaturated hydrocarbon alkynyl moieties include, but are not limited to, chemical groups such as propargyl.

The term "cycloalkyl", as used herein, refers to a monocyclic, bicyclic, tricyclic, fused, bridged, or spiro monovalent saturated hydrocarbon moiety of 3-10 carbon atoms, unless otherwise specified, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, and the like.

The compounds of the present invention may be converted to salts (e.g., pharmaceutically acceptable salts) using art recognized procedures. Salts may be formed from organic and inorganic bases, preferably alkali metal salts, for example, sodium, lithium, or potassium, when a compound of this invention contains a carboxylate or phenolic moiety, or similar moiety capable of forming base addition salts. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included.

Suitable salts derived from organic and inorganic acids include, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids, when a compound of this invention contains a basic moiety.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include salts derived from suitable inorganic and organic acids and bases that are compatible with the treatment of subjects.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention. Such compounds are useful, for example, as analytical tools, as probes in biological assays, or as therapeutic agents in accordance with the present invention.

The compounds of the invention may contain one or more asymmetric carbon atoms or one or more asymmetric (chiral) centers and may thus give rise to optical isomers and diastereomers. Thus, the invention includes such optical isomers and diastereomers; as well as the racemic and resolved, enantiomerically pure stereoisomers; as well as other mixtures of the R and S stereoisomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of formula I and/or II, the stereoisomers thereof, and the pharmaceutically acceptable salts of either of the foregoing. The compounds of the invention may be present as a mixture of stereoisomers, individual stereoisomers, or as an optically active or enantiomerically pure form.

In a specific embodiment of a compound of formula I or II:

A, B and C are selected individually or pairs from carbon or nitrogen

W=(CHR³)m
D=O
E=O or NH
F is selected from

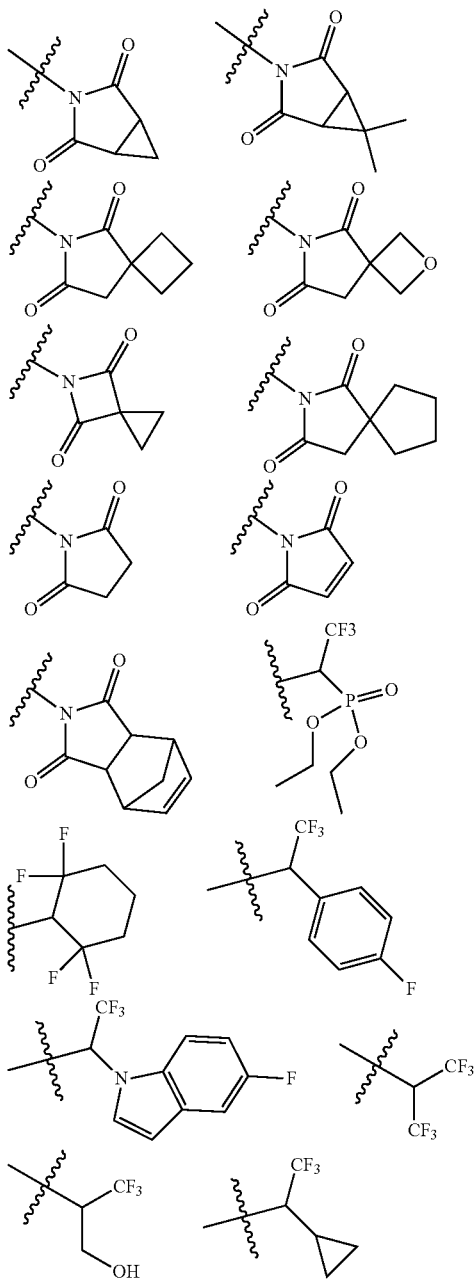

G=O, NH, NR¹³
n, m=1-2;
R¹ is selected from H, $C_1$-$C_5$alkyl group straight-chain or branched, $C_1$-$C_5$alkyl-oxy, $C_3$-$C_6$cycloalkyl, $C_3$-$C_6$cycloalkyl-oxy, $C_1$-$C_5$alkyl or $C_1$-$C_5$alkyl-oxy substituted at the terminal carbon with haloalkyl, haloalkoxy, alkoxy, $NR^8R^9$, CN, aryl, O-aryl, O-aralkyl, $NR^{10}$-aryl, $NR^{11}$-aralkyl, O-heteroaryl, $NR^{12}$-heteroaryl, saturated or unsaturated four-, five- or six-membered ring which can contain up to 2 heteroatoms selected from N, S and O;

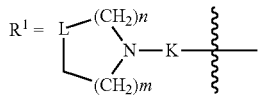

wherein
K=—(CH₂)n, —O(CH₂)n-, —(CH₂O)n, or none, when K is none the nitrogen is directly attached to the aromatic ring;
n, m=1-3;
L=CH₂, O, S, SO, SO₂, CO, NH, $NR^{14}$;
$R^2$, $R^3$ can be independently H, $C_1$-$C_5$ alkyl group straight-chain or branched, aryl, heteroaryl;
Z is selected from aryl, heteroaryl, aralkyl, heteroalkyl, $C_1$-$C_5$alkyl group straight-chain or branched, $C_1$-$C_5$alkyl-oxy, $C_3$-$C_6$cycloalkyl, $C_3$-$C_6$cycloalkyl-oxy, $C_1$-$C_5$alkyl or $C_1$-$C_5$alkyl-oxy substituted at the terminal carbon with halogen, haloalkyl, haloalkoxy, alkoxy, alkenyl, alkynyl, $NR^8R^9$, CN, aryl, O-aryl, O-aralkyl, $NR^{10}$-aryl, $NR^{11}$-aralkyl, O-heteroaryl, $NR^{12}$-heteroaryl, saturated or unsaturated four-, five- or six-membered ring which can contain up to 3 heteroatoms selected from N, S and O; saturated or unsaturated four-, five- or six-membered ring which can contain up to 3 heteroatoms selected from N, S and O;
$R^4$, $R^5$, $R^6$, $R^7$ can be independently H, $C_1$-$C_2$ alkyl;
$R^8$, $R^9$, $R^{10}$, $R^{11}$, $R^{12}$, $R^{13}$, $R^{14}$ can be independently H, $C_1$-$C_3$alkyl group straight-chain, branched, or $C_3$-$C_5$cycloalkyl;
a stereoisomer thereof; or a pharmaceutically acceptable salt thereof.

In another specific embodiment of a compound of formula I or II:
A, B and C are selected individually or pairs from carbon or nitrogen;
W=(CHR³)m;
D=O;
E=O;
F is selected from

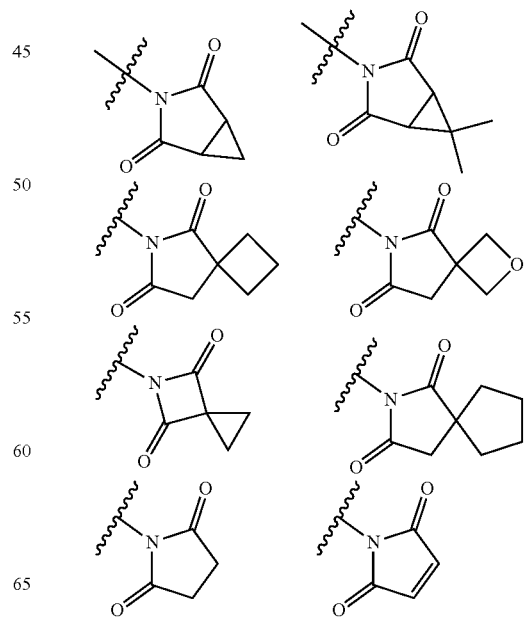

-continued n, m=1-2;
R¹ is selected from H, C₁-C₅alkyl group straight-chain or branched, C₁-C₅alkyl-oxy, C₃-C₆cycloalkyl, C₃-C₆cycloalkyl-oxy, C₁-C₅alkyl or C₁-C₅alkyl-oxy substituted at the terminal carbon with F, CF₃, OCF₃, OCHF₂, alkoxy, NR⁸R⁹, CN, aryl, O-aryl, O-aralkyl, NR¹⁰-aryl, NR¹¹-aralkyl, O-heteroaryl, NR¹²-heteroaryl, saturated or unsaturated four-, five- or six-membered ring which can contain up to 2 heteroatoms selected from N, S and O; saturated of five- or six-membered ring which can contain up to 2 heteroatoms selected from N, S and O;

$$R^1 = L\underset{(CH_2)m}{\overset{(CH_2)n}{\diagup}}N-K\diagup$$

wherein
K=—(CH₂)n, —O(CH₂)n-, —(CH₂O)n, or none, when K is none the nitrogen is directly attached to the aromatic ring;
n, m=1-3;
L=CH₂, O, S, SO, SO₂, CO, NH, NR¹⁴;
R², R³ can be independently H, C₁-C₅ alkyl group straight-chain or branched, aryl, heteroaryl;
Z is selected from aryl, heteroaryl, aralkyl, heteroalkyl, C1-C5alkyl group straight-chain or branched, C1-C5alkyl-oxy, C3-C6cycloalkyl, C3-C6cycloalkyl-oxy, C1-C5alkyl or C1-C5alkyl-oxy substituted at the terminal carbon with halogen, haloalkyl, haloalkoxy, alkoxy, alkenyl, alkynyl, NR8R9, CN, aryl, O-aryl, O-aralkyl, NR10-aryl, NR11-aralkyl, O-heteroaryl, NR12-heteroaryl, saturated or unsaturated four-, five- or six-membered ring which can contain up to 3 heteroatoms selected from N, S and O; saturated or unsaturated four-, five- or six-membered ring which can contain up to 3 heteroatoms selected from N, S and O;
R4, R5, R6, R7 can be independently H, C1-C2 alkyl;
R8, R9, R10, R11, R12, R13, R14 can be independently H, C1-C3alkyl group straight-chain, branched, or C3-C5cycloalkyl;

a stereoisomer thereof; or a pharmaceutically acceptable salt thereof.

Examples of compound of formula I include:

Example 1

1,1,1,3,3,3-Hexafluoropropan-2-yl 3,4-dihydroisoquinoline-2(1H)-carboxylate

Example 2

1,1,1,3,3,3-Hexafluoropropan-2-yl(R)-1-phenyl-3,4-dihydroisoquinoline-2(1H)-carboxylate Example 3

1,1,1,3,3,3-Hexafluoropropan-2-yl (S)-1-phenyl-3,4-dihydroisoquinoline-2(1H)-carboxylate Example 4

1,1,1,3,3,3-Hexafluoropropan-2-yl 8-bromo-3,4-dihydroisoquinoline-2(1H)-carboxylate Example 5

1,3-Difluoropropan-2-yl 5-bromo-3,4-dihydroisoquinoline-2(1H)-carboxylate

Example 6

1,1,1,3,3,3-Hexafluoropropan-2-yl 1-methyl-3,4-dihydroisoquinoline-2(1H)-carboxylate Example 7

1,1,1,3,3,3-Hexafluoropropan-2-yl 1-ethyl-3,4-dihydroisoquinoline-2(1H)-carboxylate Example 8

1,1,1,3,3,3-Hexafluoropropan-2-yl 5-bromoisoindoline-2-carboxylate

Example 9

1,1,1,3,3,3-Hexafluoropropan-2-yl 5-methoxyisoindoline-2-carboxylate

Example 10

1,1,1,3,3,3-Hexafluoropropan-2-yl 5-bromoindoline-1-carboxylate

Example 11

1,1,1,3,3,3-Hexafluoropropan-2-yl 3-bromo-5,7-dihydro-6H-pyrrolo[3,4-b]pyridine-6-carboxylate Example 12

1,1,1,3,3,3-Hexafluoropropan-2-yl 4-bromoisoindoline-2-carboxylate

Example 13

1,1,1,3,3,3-Hexafluoropropan-2-yl 3-methyl-3,4-dihydroisoquinoline-2(1H)-carboxylate

Example 14

1,1,1,3,3,3-Hexafluoropropan-2-yl-2-chloro-5,7-dihydro-6H-pyrrolo[3,4-b]pyridine-6-carboxylate

Example 15

1,1,1,3,3,3-Hexafluoropropan-2-yl 5-bromo-1-methylisoindoline-2-carboxylate

Example 16

1,1,1,3,3,3-Hexafluoropropan-2-yl 5-bromo-3,4-dihydroisoquinoline-2(1H)-carboxylate

Example 17

1,1,1,3,3,3-Hexafluoropropan-2-yl 6-bromo-3,4-dihydroisoquinoline-2(1H)-carboxylate

Example 18

1,1,1,3,3,3-Hexafluoropropan-2-yl 7-bromo-3,4-dihydroisoquinoline-2(1H)-carboxylate

Example 19

1,1,1,3,3,3-Hexafluoropropan-2-yl 4-methoxyisoindoline-2-carboxylate

Example 20

1,1,1,3,3,3-Hexafluoropropan-2-yl 4-methyl-3,4-dihydroisoquinoline-2(1H)-carboxylate

Example 21

1,1,1,3,3,3-Hexafluoropropan-2-yl 5,6-dimethoxyisoindoline-2-carboxylate

Example 22

1,1,1,3,3,3-Hexafluoropropan-2-yl 5-methoxy-3,4-dihydroisoquinoline-2(1H)-carboxylate

Example 23

1,1,1,3,3,3-Hexafluoropropan-2-yl 6-methoxy-3,4-dihydroisoquinoline-2(1H)-carboxylate

Example 24

1,1,1,3,3,3-Hexafluoropropan-2-yl 1,3,4,5-tetrahydro-2H-benzo[c]azepine-2-carboxylate

Example 25

1,1,1,3,3,3-Hexafluoropropan-2-yl 5-phenylisoindoline-2-carboxylate

Example 26

1,1,1,3,3,3-Hexafluoropropan-2-yl 5-(3-fluoro-4-methoxyphenyl)isoindoline-2-carboxylate

Example 27

1,1,1,3,3,3-Hexafluoropropan-2-yl 8-phenyl-3,4-dihydroisoquinoline-2(1H)-carboxylate

Example 28

1,1,1,3,3,3-Hexafluoropropan-2-yl 5-phenyl-3,4-dihydroisoquinoline-2(1H)-carboxylate

Example 29

1,1,1,3,3,3-Hexafluoropropan-2-yl 5-(4-methylpiperazin-1-yl)isoindoline-2-carboxylate

Example 30

1,1,1,3,3,3-Hexafluoropropan-2-yl 5-(pyrrolidin-1-yl)isoindoline-2-carboxylate

Example 31

1,1,1,3,3,3-Hexafluoropropan-2-yl 5-(1,1-dioxidothiomorpholino)isoindoline-2-carboxylate

Example 32

1,1,1,3,3,3-Hexafluoropropan-2-yl 5-morpholinoisoindoline-2-carboxylate

Example 33

1,1,1,3,3,3-Hexafluoropropan-2-yl 5-morpholino-3,4-dihydroisoquinoline-2(1H)-carboxylate

Example 34

1,1,1,3,3,3-Hexafluoropropan-2-yl 5-(piperidin-1-yl)-3,4-dihydroisoquinoline-2(1H)-carboxylate

Example 35

6,6-Dimethyl-2,4-dioxo-3-azabicyclo[3.1.0]hexan-3-yl 5-bromo-3,4-dihydroisoquinoline-2(1H)-carboxylate

Example 36

1,3-Dioxo-2-azaspiro[4.4]nonan-2-yl 5-bromo3,4-dihydroisoquinoline-2(1H)-carboxylate

Example 37

3-((5-Bromo-3,4-dihydroisoquinolin-2(1H)-yl)oxy)-3-azabicyclo[3.1.0]hexane-2,4-dione

Example 38

6,6-Dimethyl-2,4-dioxo-3-azabicyclo[3.1.0]hexan-3-yl 5-methoxyisoindoline-2-carboxylate

Example 39

6,6-Dimethyl-2,4-dioxo-3-azabicyclo[3.1.0]hexan-3-yl 5-morpholinoisoindoline-2-carboxylate

Example 40

(R)-1,1,1-trifluoro-3-hydroxypropan-2-yl 5-bromo-3,4-dihydroisoquinoline-2(1H)-carboxylate

Example 41

1,1,1,3,3,3-Hexafluoropropan-2-yl 5-(3-fluoropropoxy)-3,4-dihydroisoquinoline-2(1H)-carboxylate

Example 42

1,1,1,3,3,3-Hexafluoropropan-2-yl 5-(3-fluoropropoxy)isoindoline-2-carboxylate

Example 43

1,1,1,3,3,3-Hexafluoropropan-2-yl 5-(cyclopropylmethoxy)isoindoline-2-carboxylate

Example 44

1,1,1,3,3,3-Hexafluoropropan-2-yl 5-(2-morpholinoethoxy)isoindoline-2-carboxylate

Example 45

1,1,1,3,3,3-Hexafluoropropan-2-yl 5-(2,2-difluoroethoxy)isoindoline-2-carboxylate.

Example 46

1,1,1,3,3,3-Hexafluoropropan-2-yl 5-(2-(dimethylamino)ethoxy)isoindoline-2-carboxylate

Example 47

1,1,1,3,3,3-Hexafluoropropan-2-yl 5-((2-morpholinoethyl)amino)isoindoline-2-carboxylate

Example 48

1,1,1,3,3,3-Hexafluoropropan-2-yl 5-(2-(piperidin-1-yl)ethoxy)isoindoline-2-carboxylate

Example 49

1,1,1,3,3,3-Hexafluoropropan-2-yl 5-(2-(pyrrolidin-1-yl)ethoxy)isoindoline-2-carboxylate

Example 50

1,1,1,3,3,3-Hexafluoropropan-2-yl 5-(2-morpholino-2-oxoethoxy)isoindoline-2-carboxylate

Example 51

1,1,1,3,3,3-Hexafluoro-2-methylpropan-2-yl 5-(2-morpholinoethoxy)isoindoline-2-carboxylate,
or
a stereoisomer thereof; or a pharmaceutically acceptable salt thereof.

Examples of Formula II include:

Example 52

1,1,1,3,3,3-Hexafluoropropan-2-yl 6-(3-(trifluoromethyl)phenoxy)-2-azaspiro [3.3] heptane-2-carboxylate

Example 53

1,1,1,3,3,3-Hexafluoropropan-2-yl-6-(3-fluorophenoxy)-2-azaspiro[3.3]heptane-2-carboxylate

Example 54

1,1,1,3,3,3-Hexafluoropropan-2-yl-6-(3-methoxyphenoxy)-2-azaspiro[3.3]heptane-2-carboxylate

Example 55

1,1,1,3,3,3-Hexafluoropropan-2-yl-6-(3-phenoxyphenoxy)-2-azaspiro[3.3]heptane-2-carboxylate

Example 56

1,1,1,3,3,3-Hexafluoropropan-2-yl 6-(3-(trifluoromethoxy)phenoxy)-2-azaspiro[3.3] heptane-2-carboxylate

Example 57

1,1,1,3,3,3-Hexafluoropropan-2-yl 2-(3-fluorophenoxy)-6-azaspiro[3.4]octane-6-carboxylate

Example 58

1,1,1,3,3,3-Hexafluoropropan-2-yl 2-(3-fluorophenoxy)-6-azaspiro[3.4]octane-6-carboxylate

Example 59

1,1,1,3,3,3-Hexafluoropropan-2-yl 6-(3-fluorophenoxy)-2-azaspiro[3.4]octane-2-carboxylate

Example 60

1,1,1,3,3,3-Hexafluoropropan-2-yl 6-((5-fluoropyridin-3-yl)oxy)-2-azaspiro[3.3]heptane-2-

Example 61

1,1,1,3,3,3-Hexafluoropropan-2-yl 6-((5-fluoropyridin-3-yl)oxy)-2-azaspiro[3.4]octane-2-carboxylate

Example 62

1,1,1,3,3,3-Hexafluoropropan-2-yl 6-(benzo[d]isoxazol-6-yloxy)-2-azaspiro[3.3]heptane-2-carboxylate

Example 63

6,6-Dimethyl-2,4-dioxo-3-azabicyclo[3.1.0]hexan-3-yl 6-(3-(trifluoromethyl)phenoxy)-2-azaspiro[3.3]heptane-2-carboxylate

Example 64

6,6-Dimethyl-2,4-dioxo-3-azabicyclo[3.1.0]hexan-3-yl 6-((5-fluoropyridin-3-yl)oxy)-2-azaspiro[3.4]octane-2-carboxylate

Example 65

1,1,1,3,3,3-Hexafluoropropan-2-yl 6-((3-(trifluoromethyl)phenyl)amino)-2-azaspiro[3.3]heptane-2-carboxylate

Example 66

1,1,1,3,3,3-hexafluoropropan-2-yl 6-((3-methoxyphenyl)amino)-2-azaspiro[3.3]heptane-2-carboxylate

Example 67

1,1,1,3,3,3-Hexafluoropropan-2-yl (2r,4s)-2-(bis(4-fluorophenyl)methoxy)-6-azaspiro[3.4]octane-6-carboxylate

Example 68

1,1,1,3,3,3-Hexafluoropropan-2-yl (2s,4r)-2-(bis(4-fluorophenyl)methoxy)-6-azaspiro[3.4]octane-6-carboxylate

Example 69

1,1,1,3,3,3-hexafluoropropan-2-yl 6-(bis(4-fluorophenyl)methoxy)-2-azaspiro[3.4]octane-2-carboxylate

Example 70

1,1,1,3,3,3-Hexafluoropropan-2-yl 6-(bis(4-fluorophenyl)methoxy)-2-azaspiro[3.3]heptane-2-carboxylate

Example 71

1,1,1,3,3,3-Hexafluoropropan-2-yl 2-(benzyloxy)-6-azaspiro[3.4]octane-6-carboxylate

Example 72

1,1,1,3,3,3-hexafluoropropan-2-yl (2s,4r)-2-((bis(4-fluorophenyl)methyl)amino)-6-azaspiro[3.4]octane-6-carboxylate

Example 73

1,1,1,3,3,3-hexafluoropropan-2-yl 6-((5-methoxypyridin-3-yl)amino)-2-azaspiro[3.3]heptane-2-carboxylate

Example 74

1,1,1,3,3,3-hexafluoropropan-2-yl 6-((5-fluoropyridin-3-yl)amino)-2-azaspiro[3.3]heptane-2-carboxylate, or a stereoisomer thereof; or a pharmaceutically acceptable salt thereof.

In certain embodiments, the present invention is directed to pro-drugs. Various forms of pro-drugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

Compounds of the invention may be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic schemes. The skilled practitioner will know how to make use of variants of these reaction sequences, which in themselves are well known in the art.

Compositions

Provided herein is a composition (e.g., a pharmaceutically acceptable composition) comprising an agent that inhibits ABHD6 and/or MGL (e.g., a compound of formula I and/or II, or a stereoisomer thereof, or a pharmaceutically acceptable salt of the foregoing), and a pharmaceutically acceptable carrier. In certain embodiments, a composition of the invention is formulated for administration to a patient in need of the composition. In some embodiments, a composition of the invention is formulated for oral, intravenous, subcutaneous, intraperitoneal or dermatological administration to a patient in need thereof.

The term "pharmaceutically acceptable carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g., as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may be given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally and transdermally. Such administrations may be carried out using the present compounds, or pharmaceutically acceptable salts thereof, in lotions, creams, foams, patches, suspensions, solutions, and suppositories (rectal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

In some embodiments, compositions comprising a compound of formula I and/or II, or a stereoisomer thereof, or a pharmaceutically acceptable salt of the foregoing, can also include one or more other therapeutic agents (e.g., a chemotherapeutic agent, for example, paclitaxel, doxorubicin, 5-fluorouracil, tamoxifen, octreotide). When the compositions of this invention comprise a combination of a compound described herein and one or more other therapeutic agents, the agents should be present at dosage levels of between about 1 to 100%, and more preferably between about 5% to about 95% of the dosage normally administered in a monotherapy regimen. The additional agent(s) can be administered separately, as part of a multiple dose regimen, from the compound described herein. Alternatively, the additional agent(s) can be part of a single dosage form, mixed together with a compound described herein in a single composition.

The compositions described herein can, for example, be administered by injection, intravenously, intraarterially, intraocularly, intravitreally, subdermallym, orally, buccally, nasally, transmucosally, topically, in an ophthalmic preparation, or by inhalation, with a dosage ranging from about 0.5 mg/kg to about 100 mg/kg of body weight or, alternatively, in a dosage ranging from about 1 mg/dose to about 1000 mg/dose, every 4 to 120 hours, or according to the requirements of the particular drug. Typically, the compositions will be administered from about 1 to about 6 times per day or, alternatively, as a continuous infusion. The amount of active ingredient that can be combined with a carrier material to produce a single dosage form will vary depending upon the host treated and the particular mode of administration. A typical preparation will contain from about 5% to about 95% active compound (w/w). Alternatively, a preparation can contain from about 20% to about 80% active compound (w/w).

Doses lower or higher than those recited above may be required. Specific dosage and treatment regimens for any particular patient will depend upon a variety of factors, including the activity of the specific agent employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a subject's condition, a maintenance dose of an agent (e.g., a compound of formula I and/or II, or a stereoisomer thereof, or a pharmaceutically acceptable salt of the foregoing), composition or combination of this invention can be administered, if necessary. Subsequently, the dosage or frequency of administration, or both, can be reduced, as a function of the symptoms, to a level at which the improved condition is retained when the symptoms have been alleviated to the desired level. Subjects may, however, require intermittent treatment on a long-term basis upon recurrence of disease symptoms.

Methods

Advantageously, the compounds of formulas I and II act as ABHD6 inhibitors and/or dual ABHD6/MGL inhibitors, and can be used in methods suitable for the treatment of various diseases associated with modulation of the cannabinoid receptors through elevation of 2-AG levels in a cell, organ, or even the entire body. Most preferably, such cannabinoid receptors modulation will result in treatment and/or prevention of pain, neuropathic pain, neurodegenerative diseases including Alzheimer's disease, Parkinson's disease, amyotrophic lateral sclerosis, spinal cord injury, mental disorders such schizophrenia and depression. Thus, according to the present invention, there is provided a method of treating pain and/or a cannabinoid receptor-mediated disease or disorder in a patient in need thereof, comprising administering to the patient a therapeutically effective amount of a compound of the present invention. Cannabinoid receptor-mediated diseases and disorders include those described anywhere herein.

The present invention also provides methods for modulating (e.g., inhibiting) the activity of ABHD6 or ABHD6 and MGL, comprising administering to a patient and/or contacting a receptor of a patient (e.g., a cell) with a therapeutically effective amount of at least one compound of the invention. Certain methods further comprise determining ABHD6 or ABHD6 and MGL activity, either before or after the contacting step.

As used herein, the terms "treat," "treating," or "treatment," mean to counteract a medical condition (e.g., pain) to the extent that the medical condition is improved according to a clinically-acceptable standard.

The term "patient", as used herein, refers to a mammal, preferably a human.

The terms "administer", "administering", or "administration", as used herein, refer to either directly administering a compound or composition to a patient, or administering a pro-drug derivative or analog of the compound to the patient, which will form an equivalent amount of the active compound or substance within the patient's body.

The terms "effective amount", "therapeutically effective amount" and "effective dosage" as used herein, refer to the amount of a compound that, when administered to a patient, is effective to at least partially ameliorate (and, in some embodiments, cure) a condition from which the patient is suspected to suffer.

It is understood that the effective dosage of the active compounds of this invention may vary depending upon the particular compound utilized, the mode of administration, the condition, and severity thereof, of the condition being treated, as well as the various physical factors related to the individual being treated. For treating pain and inflammatory diseases, generally, satisfactory results may be obtained when the compounds of this invention are administered to the individual in need at a daily dosage of from about 1 mg to about 10 mg per kilogram of body weight, preferably administered in divided doses two to six times per day, or in a sustained release form. For most large mammals, the total daily dosage is from about 10 mg to about 100 mg preferably from about 5 to about 20 mg. In the case of a 70 kg human adult, the total daily dose will generally be from about 10 mg to about 150 mg and may be adjusted to provide the optimal therapeutic result. This regimen may be adjusted to provide the optimal therapeutic response.

In some embodiments, the method comprises administering an effective amount of an agent described herein in combination with one or more additional therapies (e.g., chemotherapy, radiation). When administered in a combination therapy, the agent can be administered before, after or concurrently with the other therapy (e.g., administration of a chemotherapeutic agent, such as paclitaxel or doxorubicin). When co-administered simultaneously (e.g., concurrently), the agent and other therapy can be in separate formulations or the same formulation. Alternatively, the agent and other therapy can be administered sequentially, as separate compositions, within an appropriate time frame (e.g., a cancer treatment session/interval such as about 1.5 to about 5 hours) as determined by a skilled clinician (e.g., a time sufficient to allow an overlap of the pharmaceutical effects of the therapies).

An agent described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the agent and the particular cancer to be treated. Administration can be local or systemic as indicated. The preferred mode of administration can vary depending on the particular agent chosen.

It is understood that the dosage, regimen and mode of administration of these agents will vary according to the malady and the individual being treated and will be subject to the judgment of the medical practitioner involved. It is preferred that the administration of one or more of the agents herein begin at a low dose and be increased until the desired effects are achieved.

EXEMPLIFICATION

For a more clear understanding, and in order to illustrate the invention more clearly, specific examples thereof are set forth herein below. The following examples are merely illustrative and are not to be understood as limiting the scope and underlying principles of the invention in any way.

Unless otherwise stated, all parts are parts by weight. The abbreviations TEA, DMSO and DMF refer to triethyl amine, dimethyl sulfoxide and N,N-dimethylformamide, respectively. The abbreviation TLC refers to thin layer chromatography. The abbreviation NMR refers to proton nuclear magnetic resonance and the abbreviation MS refers to mass spectroscopy, with (+) referring to the positive mode which generally gives a M+1 (or M+H) absorption, where M=the molecular mass. All compounds are analyzed at least by MS and NMR.

Proton nuclear magnetic resonance spectra were obtained on a VARIAN 400 spectrometer at 500 MHz. Spectra are given in ppm (δ) and coupling constants, J values, are reported in Hertz. Tetramethylsilane was used as an internal reference standard. Infrared spectra were obtained on a Perkin Elmer Spectrum One FT-IR spectrometer. Mass spectra were obtained on a Waters Micromass ZQ spectrometer.

Example processes are provided below in Methods A-H

Method A

Hexafluoropropan-2-yl carbamates were prepared according to Scheme 1. Triphosgene was treated with 1,1,1,3,3,3-hexafluoropropan-2-ol and an organic amine (e.g., N, N-diisopropylethylamine) to produce 1,1,1,3,3,3-hexafluoropropan-2-yl carbonochloridate, which upon treatment with amine 1 in the presence of an organic amine (e.g., N, N-diisopropylethylamine), produced carbamate 2.

Scheme 1

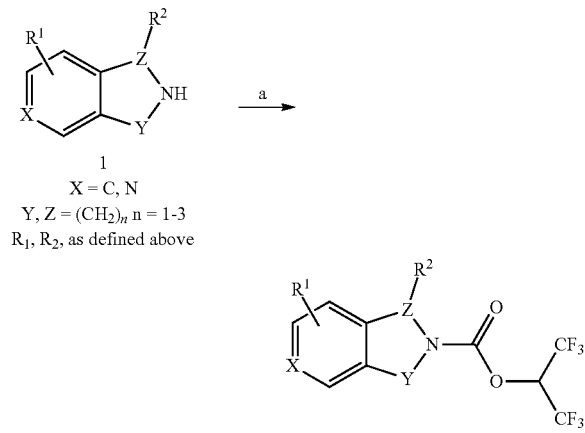

X = C, N
Y, Z = $(CH_2)_n$ n = 1-3
$R_1$, $R_2$, as defined above

Reagents: (a) 1,1,1,3,3,3-hexafluoropropan-2-ol, triphosgene, N,N-diisopropylethylamine, 0° C. to rt, 1 h The following examples were prepared according to Method A.

Example 1. 1,1,1,3,3,3-Hexafluoropropan-2-yl 3,4-dihydroisoquinoline-2(1H)-carboxylate Step a). 1,1,1,3,3,3-Hexafluoropropan-2-yl 3,4-dihydroisoquinoline-2(1H)-carboxylate triphosgene (233 mg, 0.78 mmol) was added into a cold (0° C.) solution of 1,1,1,3,3,3-hexafluoropropan-2-ol (378 mg, 2.25 mmol), and N, N-diisopropylethylamine (0.58 mL, 4.50 mmol) in dichloromethane (5 mL). The reaction mixture was gradually allowed to come to room temperature and stirred for 30 minutes. Next, the resulting solution was added dropwise into cold (0° C.) solution of 1,2,3,4-tetrahydroisoquinoline (100 mg, 0.75 mmol) and N, N-diisopropylethylamine (0.29 mL, 1.50 mmol) in dichloromethane (5 mL). The reaction mixture was gradually allowed to come to room temperature and stirred for 1 hour. Then, the reaction was diluted in dichloromethane (25 mL) and washed with water (2×15 mL) and brine. The organic extracts were dried over anhydrous $Na_2SO_4$. The solvents were removed under vacuum and the residue was purified on silica gel (Biotage; eluting solvents hexanes:EtOAc 5/1 ratio) to afford 1,1,1,3,3,3-hexafluoropropan-2-yl 3,4-dihydroisoquinoline-2(1H)-carboxylate as colorless oil (220 mg, 90% yield): $^1$H NMR (400 MHz, $CDCl_3$) δ ppm 7.23-7.15 (m, 5H), 5.80 (sept, 1H), 4.68 (m, 2H), 3.76 (t, J=6 Hz, 2H), 2.93-2.88 (m, 2H).

Example 2. 1,1,1,3,3,3-Hexafluoropropan-2-yl(R)-1-phenyl-3,4-dihydroisoquinoline-2(1H)-carboxylate $^1$H NMR (400 MHz, $CDCl_3$) δ ppm 7.32-7.02 (m, 9H), 6.43 (s, 1H), 5.85 (sept, 1H), 4.18-4.14 (m, 1H), 4.04-3.99 (m, 1H), 3.40 (ddd, $J_1$=4.4 Hz, $J_2$=10.8 Hz, $J_3$=24 Hz, 2H), 3.11-2.94 (m, 2H).

Example 3. 1,1,1,3,3,3-Hexafluoropropan-2-yl (S)-1-phenyl-3,4-dihydroisoquinoline-2(1H)-carboxylate $^1$H NMR (400 MHz, $CDCl_3$) δ ppm 7.32-7.02 (m, 9H), 6.43 (s, 1H), 5.85 (sept, 1H), 4.18-4.14 (m, 1H), 4.04-3.99 (m, 1H), 3.40 (ddd, $J_1$=4.4 Hz, $J_2$=10.8 Hz, $J_3$=24 Hz, 2H), 3.11-2.94 (m, 2H).

Example 4. 1,1,1,3,3,3-Hexafluoropropan-2-yl 8-bromo-3,4-dihydroisoquinoline-2(1H)-carboxylate $^1$H NMR (400 MHz, $CDCl_3$) δ ppm 7.45 (d, J=7.2 Hz, 1H), 7.12-7.08 (m, 2H), 5.84-5.78 (sept, 1H), 4.65 (d, J=5.2 Hz, 2H), 3.77-3.74 (m, 2H), 2.93-2.88 (m, 2H).

Example 5. 1,3-Difluoropropan-2-yl 5-bromo-3,4-dihydroisoquinoline-2(1H)-carboxylate For the preparation of Example 5, 1,3-difluoropropan-2-ol was used to generate the desired 1,3-difluoropropan-2-yl carbonochloridate, which upon reaction with 5-bromo-isoquinoline, as described in Method A, produced the final product.

$^1$H NMR (400 MHz, $CDCl_3$) 7.46-7.44 (m, 1H), 7.08-7.06 (m, 2H), 5.18-5.10 (m, 1H), 4.71-4.69 (m, 2H), 4.64 (m, 2H), 4.59-4.57 (m, 2H), 3.74 (t, J=6 Hz, 2H), 2.89 (t, J=5.6 Hz, 2H).

Example 6. 1,1,1,3,3,3-Hexafluoropropan-2-yl 1-methyl-3,4-dihydroisoquinoline-2(1H)-carboxylate (Racemic mixture 1:1): $^1$H NMR (400 MHz, $CDCl_3$) 7.24-7.12 (m, 4H), 5.87-5.80 (m, 1H), 5.27-5.19 (m, 1H), 4.20-4.06 (m, 1H), 3.49-3.34 (m, 1H), 3.03-2.90 (m, 1H), 2.85-2.79 (m, 1H), 1.53 (s, 3H).

Example 7. 1,1,1,3,3,3-Hexafluoropropan-2-yl 1-ethyl-3,4-dihydroisoquinoline-2(1H)-carboxylate (Racemic mixture 1:1): $^1$H NMR (400 MHz, $CDCl_3$) 7.21-7.11 (m, 4H), 5.85-5.79 (m, 1H), 5.09-4.97 (m, 1H), 4.20-4.07 (m, 1H), 3.41-3.35 (m, 1H), 3.04-2.79 (m, 2H), 1.89-1.80 (m, 2H), 1.00-0.95 (m, 3H).

Example 8. 1,1,1,3,3,3-Hexafluoropropan-2-yl 5-bromoisoindoline-2-carboxylate $^1$H NMR (400 MHz, $CDCl_3$) 7.45-7.41 (m, 2H), 7.18-7.12 (m, 1H), 5.80 (sept, 1H), 4.80-4.76 (m, 4H).

Example 9. 1,1,1,3,3,3-Hexafluoropropan-2-yl 5-methoxyisoindoline-2-carboxylate $^1$H NMR (500 MHz, $CDCl_3$) δ ppm 6.47 (dd, J=17, 8.5 Hz, 1H), 6.16 (d, J=8.0 Hz, 1H); 6.10 (d, J=13.5 Hz, 1H), 5.09 (sept, 1H), 4.07 (m, 4H), 3.1 (s, 3H).

Example 10. 1,1,1,3,3,3-Hexafluoropropan-2-yl 5-bromoindoline-1-carboxylate $^1$H NMR (500 MHz, CDCl$_3$) δ ppm 7.71 (d, J=9 Hz, 1H), 7.36 (m, 2H), 5.84 (sept, 1H), 4.17 (t, J=9.0 Hz, 2H), 3.21 (t, J=9.0 Hz, 2H).

Example 11. 1,1,1,3,3,3-Hexafluoropropan-2-yl 3-bromo-5,7-dihydro-6H-pyrrolo[3,4-b]pyridine-6-carboxylate $^1$H NMR (500 MHz, CDCl$_3$) δ ppm 8.60 (s, 1H), 7.78 (d, J=22 Hz, 1H), 5.80 (sept, 1H), 4.86 (d, J=13 Hz, 2H), 4.76 (s, 2H); MS (ES) m/z 393.34 [M+1]$^+$.

Example 12. 1,1,1,3,3,3-Hexafluoropropan-2-yl 4-bromoisoindoline-2-carboxylate $^1$H NMR (500 MHz, CDCl$_3$) δ ppm 7.46 (t, J=4 Hz, 1H), 7.21 (m, 2H), 5.80 (sept, 1H), 4.92 (t, J=8 Hz, 2H), 4.78 (s, J=8 Hz, 2H).

Example 13. 1,1,1,3,3,3-Hexafluoropropan-2-yl 3-methyl-3,4-dihydroisoquinoline-2(1H)-carboxylate $^1$H NMR (500 MHz, CDCl$_3$) δ ppm 7.25 (m, 2H), 7.16 (m, 2H), 5.84 (sept, 1H), 4.79 (m, 1H), 4.66-4.59 (m, 1H), 4.46 (d, J=16.5 Hz, 1H), 3.15 (m, 1H), 2.67 (d, J=16.5 Hz, 1H), 1.55 (d, J=16.5 Hz, 1H).

Example 14. 1,1,1,3,3,3-Hexafluoropropan-2-yl-2-chloro-5,7-dihydro-6H-pyrrolo[3,4-b]pyridine-6-carboxylate $^1$H NMR (500 MHz, CDCl$_3$) δ ppm 7.61 (dd, J=15, 7.5 Hz, 1H), 7.31 (d, J=8.5 Hz, 1H), 5.80 (sept, 1H), 4.86 (m, 1H), 4.82 (m, 3H).

Example 15. 1,1,1,3,3,3-Hexafluoropropan-2-yl 5-bromo-1-methylisoindoline-2-carboxylate $^1$H NMR (500 MHz, CDCl$_3$) δ ppm 7.46 (m, 1H), 7.12 (dd, J=11.5, 8 Hz, 1H), 5.82 (sept, 1H), 5.16 (m, 1H), 4.84-4.74 (m, 2H), 1.56-1.51 (m, 3H).

Example 16. 1,1,1,3,3,3-Hexafluoropropan-2-yl 5-bromo-3,4-dihydroisoquinoline-2(1H)-carboxylate $^1$H NMR (500 MHz, CDCl$_3$) δ ppm 7.48 (m, 2H), 7.14 (m, 2H), 5.81 (sept, 1H), 4.68 (m, 2H), 3.8 (m, 2H), 2.94 (m, 2H).

Example 17. 1,1,1,3,3,3-Hexafluoropropan-2-yl 6-bromo-3,4-dihydroisoquinoline-2(1H)-carboxylate $^1$H NMR (500 MHz, CDCl$_3$) δ ppm 7.34 (m, 2H), 7.02 (d, J=8 Hz, 1H), 5.81 (sept, 1H), 4.62 (m, 2H), 3.75 (t, J=6.5 Hz, 2H), 2.89 (m, 2H).

Example 18. 1,1,1,3,3,3-Hexafluoropropan-2-yl 7-bromo-3,4-dihydroisoquinoline-2(1H)-carboxylate $^1$H NMR (500 MHz, CDCl$_3$) δ ppm 7.34 (d, J=8 Hz, 1H), 7.31 (d, J=4.5 Hz, 1H), 7.05 (dd, J=8, 3.4 Hz, 1H), 5.81 (sept, 1H), 4.66 (m, 2H), 3.76 (m, 2H), 2.86 (m, 2H).

Example 19. 1,1,1,3,3,3-Hexafluoropropan-2-yl 4-methoxyisoindoline-2-carboxylate $^1$H NMR (500 MHz, CDCl$_3$) δ ppm 7.29 (m, 1H), 6.87 (dd, J=4.5, 17.5, 7 Hz, 1H), 6.79 (d, J=8.5 Hz, 1H), 5.81 (sept, 1H), 4.82 (m, 2H), 4.76 (m, 2H).

Example 20. 1,1,1,3,3,3-Hexafluoropropan-2-yl 4-methyl-3,4-dihydroisoquinoline-2(1H)-carboxylate $^1$H NMR (500 MHz, CDCl$_3$) δ ppm 7.23-7.21 (m, 3H), 5.83 (sept, 1H), 4.92, 4.83 (doublets of isomers, J=16.5, 16.5 Hz, 1H), 4.62 and 4.52 (doublets of isomers, J=16.5, 16.5 Hz, 1H), 3.79 and 3.76 (doublets of isomers, J=5.0, 5.0 Hz, 1H), 3.66 (t, J=5.5 Hz, 1H), 3.61 and 3.59 (doublets of isomers, J=4.5, 4.5 Hz, 1H), 3.05 (m, 1H), 1.3 and 1.29 (doublets of isomers, J=6.0, 5.5 Hz, 3H).

Example 21. 1,1,1,3,3,3-Hexafluoropropan-2-yl 5,6-dimethoxyisoindoline-2-carboxylate $^1$H NMR (400 MHz, CDCl$_3$) δ ppm 6.78 (d, J=11.6 Hz, 2H), 5.83 (sept, J=6.4 Hz, 1H), 4.77 (d, J=3.6 Hz, 4H), 3.89 (d, J=5.6 Hz, 6H).

Example 22. 1,1,1,3,3,3-Hexafluoropropan-2-yl 5-methoxy-3,4-dihydroisoquinoline-2(1H)-carboxylate $^1$H NMR (500 MHz, CDCl$_3$) δ ppm 7.21 (m, 1H), 6.75 (d, J=7.5 Hz, 2H), 5.83 (sept, 1H), 4.67 (s, 2H), 3.84 (d, J=1.5 Hz, 3H), 3.77-3.74 (m, 2H), 2.85-2.81 (m, 2H).

Example 23. 1,1,1,3,3,3-Hexafluoropropan-2-yl 6-methoxy-3,4-dihydroisoquinoline-2(1H)-carboxylate $^1$H NMR (500 MHz, CDCl$_3$) δ ppm 7.07 (dd, J=2.5, 11.5 Hz, 1H), 6.81-6.78 (m, 1H), 6.70 (s, 1H), 5.81 (sept, J=6 Hz, 1H), 4.62 (d, J=3.5 Hz, 2H), 3.79 (s, 3H), 3.75 (t, J=6 Hz, 2H), 2.90 (m, 2H).

Example 24. 1,1,1,3,3,3-Hexafluoropropan-2-yl 1,3,4,5-tetrahydro-2H-benzo[c]azepine-2-carboxylate $^1$H NMR (400 MHz, CDCl$_3$) δ ppm 7.19-7.14 (m, 4H), 5.688 (sept, J=6.4 Hz, 1H), 4.52 (d, J=10 Hz, 2H), 3.81-3.76 (m, 2H), 3.00-2.95 (m, 2H), 1.87-1.80 (m, 2H).

Method B

Aryl-substituted compounds 3 were prepared according to Scheme 2. Palladium mediated cross-coupling reaction between aryl-bromide 1 and the appropriate boronic acids were used to generate the biphenyl analogs 2. Palladium catalysts suitable for use in the process of the invention include Pd(0) or Pd(II) catalysts such as dichlorobis(tri-o-tolylphosphine)palladium(II), tetrakis(triphenylphosphine)palladium(0), or the like. Inorganic bases suitable for use in the inventive process include Na or K hydroxides, carbonates or bicarbonates, preferably Na$_2$CO$_3$ or K$_2$CO$_3$. Solvents suitable for use in the inventive process include polar or non-polar organic solvents such as toluene, dioxane. Carbamates 3 were produced as described in Method A.

Scheme 2

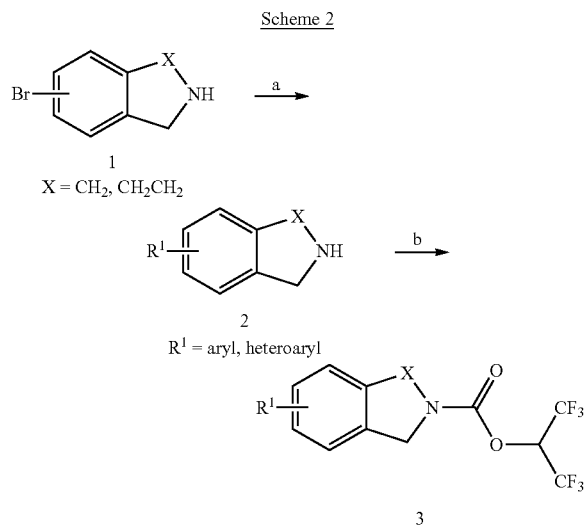

Reagents: (a) Aryl-B(OH)₂, Pd(PPh₃)₄, K₂CO₃; (b) 1,1,1,3,3,3-hexafluoropropan-2-ol, triphosgene, N,N-diisopropylethylamine, 0° C. to rt, 1 h The following examples were prepared according to Method B.

Example 25. 1,1,1,3,3,3-Hexafluoropropan-2-yl 5-phenylisoindoline-2-carboxylate

Step a). 5-Phenylisoindoline

Into a microwave vessel were added 5-bromoisoindoline hydrochloride (110.3 mg, 0.47 mmol), benzeneboronic acid (114.7 mg, 0.94 mmol), K₂CO₃ (259.4 mg, 1.88 mmol), dioxane (8 mL) and water (2 mL). Argon gas was passed through the mixture for 10 minutes and then tetrakis(triphenylphosphine)palladium(0) (5.42 mg 0.0047 mmol) was added and the argon flow continued for 5 additional minutes. Then, the vessel was sealed and microwaved at 110° C. for 2 hours. The mixture was diluted with EtOAc (30 mL) and washed with water and brine. The organics extracts were dried over anhydrous MgSO₄. The solvents were removed under vacuum and the product 5-phenylisoindoline (91.8 mg) was carried to the next step without further purification.

Step b). 1,1,1,3,3,3-Hexafluoropropan-2-yl 5-phenylisoindoline-2-carboxylate This step was performed according to Method A.

$^1$H NMR (500 MHz, CDCl₃) δ ppm 7.58-7.54 (m, 3H), 7.51-7.44 (m, 3H), 7.39-7.33 (m, 3H), 5.82 (sept, 1H), 4.88 (m, 4H).

Example 26. 1,1,1,3,3,3-Hexafluoropropan-2-yl 5-(3-fluoro-4-methoxyphenyl)isoindoline-2-carboxylate This compound was prepared according to Example 21 using (3-fluoro-4-methoxyphenyl)boronic acid.

$^1$H NMR (500 MHz, CDCl₃) δ ppm 7.4 (dd, J=7.5, 2.0 Hz, 1H), 7.44 (d, J=18.5 Hz, 1H), 7.36-7.29 (m, 3H), 7.05 (dt, J=8.5, 1.5 Hz, 1H), 5.82 (sept, 1H), 4.87 (m, 4H), 3.94 (s, 3H).

Example 27. 1,1,1,3,3,3-Hexafluoropropan-2-yl 8-phenyl-3,4-dihydroisoquinoline-2(1H)-carboxylate $^1$H NMR (500 MHz, CDCl₃) δ ppm 7.44-7.35 (m, 3H), 7.31-7.25 (m, 3H), 7.19-7.14 (m, 2H), 5.72 (sept, 1H), 4.54 (m, 2H), 3.77-3.71 (m, 2H), 3.02-2.97 (m, 2H).

Example 28. 1,1,1,3,3,3-Hexafluoropropan-2-yl 5-phenyl-3,4-dihydroisoquinoline-2(1H)-carboxylate $^1$H NMR (500 MHz, CDCl₃) δ ppm 7.46-7.16 (m, 8H), 5.84-7.79 (sept, 1H), 4.75 (d, J=7 Hz, 2H), 3.66-3.64 (m, 2H), 2.84-2.81 (m, 2H).

Method C

Heterocyclic N-substituted compounds which contain one or more of N, O, S, and SO₂ were prepared according to Scheme 3. Palladium mediated cross-coupling reaction between aryl-bromide 1 and the appropriate amine 2 was used to generate the N-substituted analogs 3. Palladium catalysts suitable for use in the process of the invention include Pd₂(dba)₃, 2-(di-tert-butylphosphino)biphenyl, 2,2'-bis(diphenylphosphino)-1,1'-binaphthalene and the like. Solvents suitable for use in the inventive process include polar or non-polar organic solvents such as toluene, benzene. Deprotection of the BOC group with trifluoroacetic acid to amine 4 and subsequent carbamate formation as described in Method A produced carbamate 5.

Scheme 3

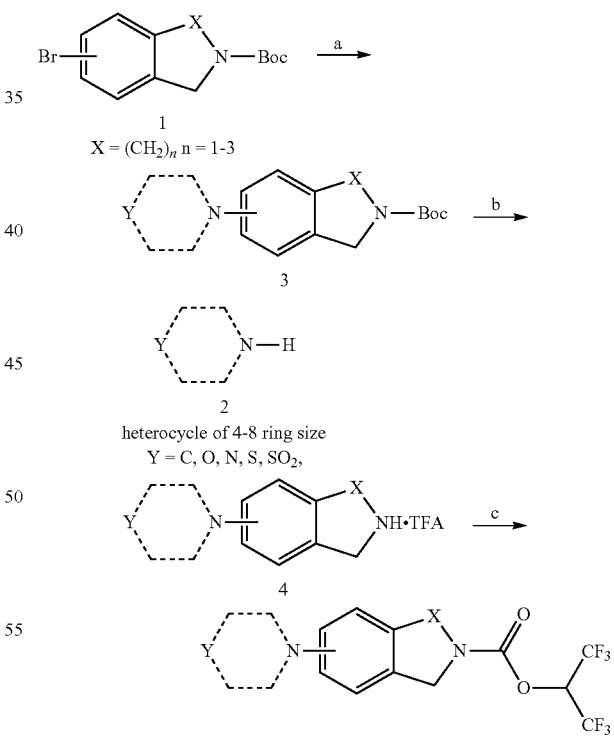

Reagents: (a) Pd₂(dba)₃, 2-(di-tert-butylphosphino)biphenyl, sodium tert-butoxide, N-heterocycle (i.e N-methylpiperazine), toluene, 80° C.; (b) TFA, dichloromethane: (c) 1,1,1,3,3,3-hexafluoropropan-2-ol, triphosgene, N,N-diisopropylethylamine, 0° C. to rt, 1 h The following examples were prepared according to Method C.

Example 29. 1,1,1,3,3,3-Hexafluoropropan-2-yl 5-(4-methylpiperazin-1-yl)isoindoline-2-carboxylate Step a). tert-butyl 5-(4-methylpiperazin-1-yl)isoindoline-2-carboxylate Tris(dibenzylideneacetone)dipalladium(0) (228 mg, 0.25 mmol), 2-(di-tert-butylphosphino)biphenyl (149 mg, 0.50 mmol) and sodium tert-butoxide (1.34 g, 13.9 mmol) were added into a solution of 5-bromo-1,3-dihydro-isoindole-2-carboxylic acid tert-butyl ester (2.97 g, 10 mmol) in toluene (15 mL). The reaction mixture was purged with argon for 5 minutes and then N-methylpiperazine (1.33 mL, 12 mmol) was added and the mixture and stirred at 80° C. for 4 hours. After the completion of the reaction (monitored by TLC) the solvent was removed under vacuum, water (3 mL) was added, and the reaction mixture was extracted with dichloromethane (3×30 mL). The combined organic extracts were dried over $Na_2SO_4$. The solvents were removed under vacuum and the residue was purified on silica gel (Biotage; eluting solvents 5% MeOH in dichloromethane) to afford tert-butyl 5-(4-methylpiperazin-1-yl)isoindoline-2-carboxylate as brown solid (1.75 g, 55% yield); $^1$H NMR (400 MHz, MeOH-$d_4$) δ ppm 7.16-7.12 (m, 1H), 6.92-6.88 (m, 2H), 4.59-4.53 (m, 4H), 3.19-3.17 (m, 4H), 2.63-2.60 (m, 4H), 2.34 (s, 3H), 1.51 (9H, s).

Step b). 5-(4-Methylpiperazin-1-yl)isoindoline.TFA

Trifluoroacetic acid (0.6 mL, 16.08) was slowly added into a cold (0° C.) solution of tert-butyl 5-(4-methylpiperazin-1-yl)isoindoline-2-carboxylate (1.7 g, 5.36 mmol) and dichloromethane (25 mL). The resulting reaction mixture was stirred at room temperature for 2 hours. Then, the mixture was concentrated under vacuum and $CHCl_3$ (2×15 mL) was added and evaporated to ensure removal of the trifluoroacetic acid. The product 5-(4-methylpiperazin-1-yl)isoindoline.TFA was used in the next step without any further purification.

Step c). 1,1,1,3,3,3-Hexafluoropropan-2-yl 5-(4-methylpiperazin-1-yl)isoindoline-2-carboxylate Triphosgene (50 mg, 0.17 mmol) was added into a cold (0° C.) solution of 1,1,1,3,3,3-hexafluoropropan-2-ol (80 mg, 0.47 mmol), N,N-diisopropylethylamine (0.18 mL, 1.42 mmol) and dichloromethane (5 mL). The reaction mixture was allowed to come to room temperature and stirred for 30 minutes. The resulting solution was added dropwise into cold (0° C.) solution of 5-(4-methylpiperazin-1-yl)isoindoline.TFA (50 mg, 0.16 mmol) and N,N-diisopropylethylamine (0.06 mL, 0.476 mmol) in dichloromethane (5 mL). The reaction mixture was allowed to come to room temperature and stirred for 1 hour. Then, the reaction was diluted in dichloromethane (25 mL) and washed with water (2×15 mL) and brine. The organic extracts were dried over anhydrous $Na_2SO_4$. The solvents were removed under vacuum and the residue was purified on silica gel (Biotage; eluting solvents dichloromethane:MeOH 10/1 ratio) to afford 1,1,1,3,3,3-hexafluoropropan-2-yl 5-(4-methylpiperazin-1-yl)isoindoline-2-carboxylate as brown solid (38 mg, 60% yield); $^1$H NMR (400 MHz, $CDCl_3$) δ ppm 7.18-7.13 (m, 1H), 6.91-6.90 (m, 1H), 6.88-6.80 (m, 1H), 5.80 (sept, 1H), 4.77-4.73 (m, 4H), 3.28-3.27 (m, 4H), 2.77 (s, 4H), 2.48 (s, 3H).

Example 30. 1,1,1,3,3,3-Hexafluoropropan-2-yl 5-(pyrrolidin-1-yl)isoindoline-2-carboxylate $^1$H NMR (400 MHz, $CDCl_3$) δ ppm 7.12-7.06 (m, 1H), 6.53-6.50 (m, 1H), 6.43-6.40 (m, 1H), 5.80 (sept, 1H), 4.76-4.71 (m, 4H), 3.28-3.26 (m, 4H), 2.03-2.00 (m, 4H).

Example 31. 1,1,1,3,3,3-Hexafluoropropan-2-yl 5-(1,1-dioxidothiomorpholino)isoindoline-2-carboxylate $^1$H NMR (500 MHz, $CDCl_3$) δ ppm 7.23-7.18 (m, 1H), 6.91-6.88 (m, 1H), 6.85 (d, J=14.5 Hz, 1H), 5.81-5.78 (sept, 1H), 4.79 (d, J=11 Hz, 2H), 4.77 (d, J=8.5 Hz, 2H) 3.85-3.3.82 (m, 4H), 3.13-3.11 (m, 4H); MS (ES) m/z 347.46 $[M+1]^+$.

Example 32. 1,1,1,3,3,3-Hexafluoropropan-2-yl 5-morpholinoisoindoline-2-carboxylate $^1$H NMR (500 MHz, $CDCl_3$) δ ppm 7.20-7.15 (m, 1H), 6.90-6.87 (m, 1H), 6.82 (d, J=15.5 Hz, 1H), 5.81-5.79 (sept, 1H), 4.78 (dd, J=7.5, 4.5 Hz, 4H), 3.88 (t, J=5 Hz, 4H), 3.16-3.13 (m, 4H); MS (ES) m/z 399.49 $[M+1]^+$.

Example 33. 1,1,1,3,3,3-Hexafluoropropan-2-yl 5-morpholino-3,4-dihydroisoquinoline-2(1H)-carboxylate $^1$H NMR (500 MHz, $CDCl_3$) δ ppm 7.25-7.12 (m, 1H), 6.90-6.87 (dd, J=7.5, 3.5 Hz, 1H), 6.82 (t, J=7.5 Hz, 1H), 5.83-5.81 (sept, 1H), 4.68 (d, J=8 Hz, 2H), 3.86-3.84 (m, 4H), 3.72 (t, J=6 Hz, 2H), 2.94-2.89 (m, 6H); MS (ES) m/z 413.5 $[M+1]^+$.

Example 34. 1,1,1,3,3,3-Hexafluoropropan-2-yl 5-(piperidin-1-yl)-3,4-dihydroisoquinoline-2(1H)-carboxylate $^1$H NMR (500 MHz, $CDCl_3$) δ ppm 7.21 (t, J=8 Hz, 1H), 6.95-6.93 (m, 1H), 6.86 (t, J=8.5 Hz, 1H), 5.84-5.81 (sept, 1H), 4.67 (d, J=10 Hz, 2H), 3.71-3.68 (m, 2H), 2.93-2.89 (m, 2H), 2.83 (brs, 4H), 1.73-1.69 (m, 4H), 1.59-1.55 (m, 2H); MS (ES) m/z 411.55 $[M+1]^+$.

Method D

Imide-type carbamates 5 were prepared according to Scheme 4. The required hydroxylamines 3 were prepared from lactones 1 upon treatment with O-benzylhydroxylamine in the presence of an organic base, e.g., N-methylmorpholine, and acetic acid to produce 2, followed by catalytic hydrogenation (e.g., $H_2$, Pd/C). Hydroxylamines 3 were coupled with amines 4 in a similar manner as described in Method A.

Scheme 4

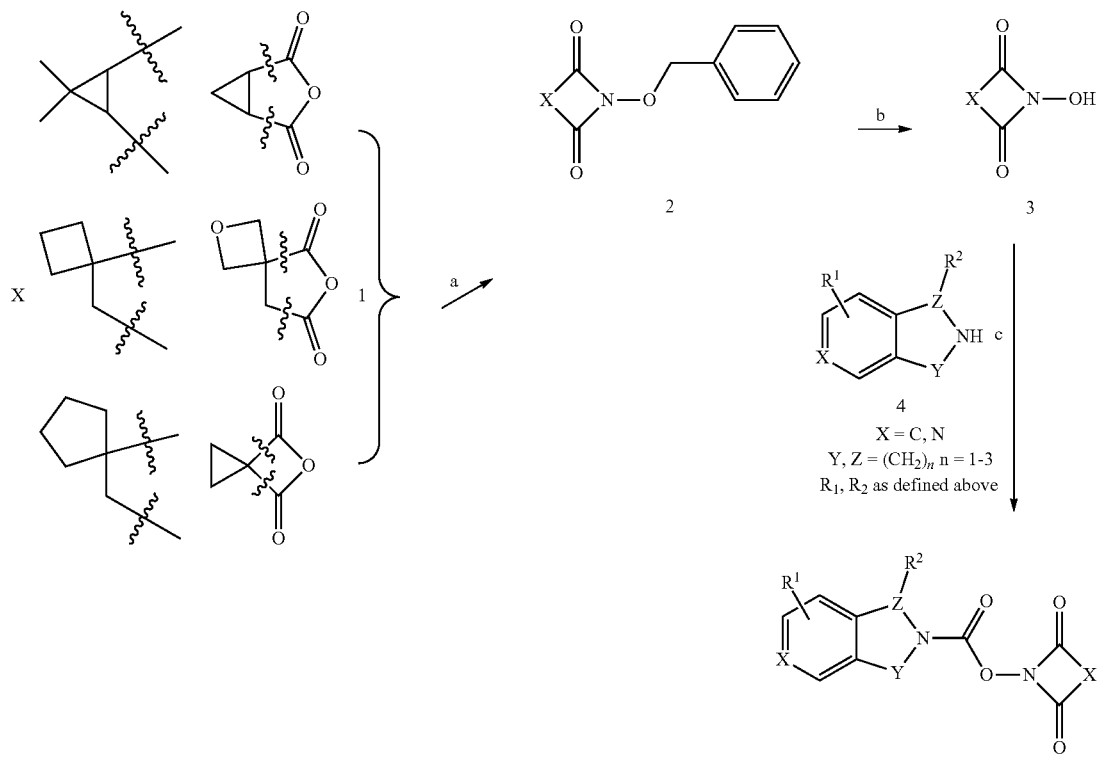

Reagents: (a) O-benzylhydroxylamine hydrochloride, N-methylmorpholine, AcOH, toluene, 110° C., 8 h; (b) H₂, Pd/C, 1:1 MeOH/EtOAc, 24 h; (c) amine 4 (i.e. 5-bromo-1,2,3,4-tetrahydroisoquinoline), triphosgene, N,N-diisopropylethylamine, 0° C. to rt, 1 h The following examples were prepared according to Method D Example 35. 6,6-Dimethyl-2,4-dioxo-3-azabicyclo[3.1.0]hexan-3-yl 5-bromo-3,4-dihydroisoquinoline-2(1H)-carboxylate Step a). 3-(Benzyloxy)-6,6-dimethyl-3-azabicyclo[3.1.0]hexane-2,4-dione O-benzylhydroxylamine hydrochloride (0.79 g, 5 mmol) was added into a solution of 6,6-dimethyl-3-oxabicyclo[3.1.0]hexane-2,4-dione (0.7 g, 5 mmol), N-methylmorpholine (1.01 mL, 10 mmol) and anhydrous toluene (30 mL). The resulting reaction mixture was stirred at room temperature for 30 minutes and then heated to reflux with azeotropic removal of water using Dean-Stark apparatus. Glacial acetic acid (1.0 mL) was added after 2 hours into the mixture and the reaction refluxed additionally for 6 hours. Then, the reaction mixture was allowed to come to room temperature, and the product was extracted with ethyl acetate (3×50 mL) and washed with saturated solution of NaHCO₃ and brine. The combined organic layers were dried over anhydrous Na₂SO₄. The solvents were removed under vacuum and the residue was purified on silica gel (Biotage; eluting solvents dichloromethane:MeOH 10/1 ratio) to afford 3-(benzyloxy)-6,6-dimethyl-3-azabicyclo[3.1.0]hexane-2,4-dione as a white solid (720 mg, 59% yield); $^1$H NMR (400 MHz, CDCl₃) δ ppm 7.50-7.48 (m, 2H), 7.38-7.36 (m, 3H), 5.08 (s, 2H), 1.24 (s, 3H), 1.20 (s, 3H).

Step b). 3-Hydroxy-6,6-dimethyl-3-azabicyclo[3.1.0]hexane-2,4-dione. 10% Pd/C (70 mg) was added into a solution of 3-(benzyloxy)-6,6-dimethyl-3-azabicyclo[3.1.0]hexane-2,4-dione (700 mg, 2.85 mmol) in 1:1 ethyl acetate/methanol (20 mL). The resulting reaction mixture was stirred at room temperature under a hydrogen atmosphere for 24 hours. The reaction mixture was filtered through a celite pad. The filtrate was concentrated under reduced pressure to afford 3-hydroxy-6,6-dimethyl-3-azabicyclo[3.1.0]hexane-2,4-dione as colorless solid (430 mg, 97% yield) which was used to the next step without any further purification.

Step c). 6,6-dimethyl-2,4-dioxo-3-azabicyclo[3.1.0]hexan-3-yl 5-bromo-3,4-dihydroisoquinoline-2(1H)-carboxylate. Triphosgene (37 mg, 0.12 mmol) was added into a cold (0° C.) solution of 3-hydroxy-6,6-dimethyl-3-azabicyclo[3.1.0]hexane-2,4-dione (55 mg, 0.36 mmol), N,N-diisopropylethylamine (0.06 mL, 0.47 mmol) and dichloromethane (3 mL). The reaction mixture was allowed to come to room temperature and stirred for 30 minutes. The resulting solution was added dropwise into a cold (0° C.) solution of 5-bromo-1,2,3,4-tetrahydroisoquinoline (50 mg, 0.24 mmol), N,N-diisopropylethylamine (0.06 mL, 0.47 mmol) and dichloromethane (3 mL). The reaction mixture was allowed to come to room temperature and stirred for 1 hour. Then, the reaction was diluted in dichloromethane (25 mL) and washed with water (2×15 mL) and brine. The organic extracts were dried over anhydrous NaSO₄. The solvents were removed under vacuum and the residue was purified on silica gel (Biotage; eluting solvents hexanes:EtOAc 3/1 ratio) to afford 6,6-dimethyl-2,4-dioxo-3-azabicyclo[3.1.0]hexan-3-yl 5-bromo-3,4-dihydroisoquinoline-2

(1H)-carboxylate as colorless solid (56 mg, 65% yield); $^1$H NMR (400 MHz, CDCl$_3$) δ ppm 7.48-7.46 (m, 1H), 7.10-7.04 (m, 2H), 4.75-4.63 (m, 2H), 3.83-3.74 (m, 2H), 2.99-2.95 (m, 2H).

Example 36. 1,3-Dioxo-2-azaspiro[4,4]nonan-2-yl 5-bromo3,4-dihydroisoquinoline-2(1H)-carboxylate $^1$H NMR (400 MHz, CDCl$_3$) δ ppm 7.47 (d, J=8.4 Hz, 1H), 7.09-7.06 (m, 2H), 4.80 (brs, 1H), 4.64 (brs, 1H), 3.87 (brs, 1H), 3.76 (brs, 1H), 3.01-2.96 (m, 2H), 2.69 (s, 2H), 2.22-2.18 (m, 2H), 1.94-1.93 (m, 2H), 1.78-1.74 (m, 4H).

Example 37. 3-((5-Bromo-3,4-dihydroisoquinolin-2(1H)-yl)oxy)-3-azabicyclo[3.1.0]hexane-2,4-dione $^1$H NMR (400 MHz, CDCl$_3$) δ ppm 7.48-7.46 (m, 1H), 7.08-7.04 (m, 2H), 4.57 (brs, 1H), 4.60 (brs, 1H), 3.83-3.71 (m, 2H), 3.00-2.94 (m, 2H), 2.50-2.47 (m, 2H), 1.64-1.60 (m, 2H).

Example 38. 6,6-Dimethyl-2,4-dioxo-3-azabicyclo[3.1.0]hexan-3-yl 5-methoxyisoindoline-2-carboxylate $^1$H NMR (500 MHz, CDCl$_3$) δ ppm 7.18-7.12 (m, 1H), 6.86-6.75 (m, 2H), 4.85 (d, J=12.8 Hz, 2H), 4.75 (d, J=13.6 Hz, 2H), 3.80 (s, 3H), 2.34 (s, 2H), 1.29 (s, 6H).

Example 39. 6,6-Dimethyl-2,4-dioxo-3-azabicyclo[3.1.0]hexan-3-yl 5-morpholinoisoindoline-2-carboxylate Step a) 4-(isoindolin-5-yl) morpholine.TFA salt was synthesized according to Method C, step a).

Step b) The imide-type carbamate was synthesized according to Method D, step c). $^1$H NMR (500 MHz, CDCl$_3$) δ ppm 7.13 (dd, J=17.9, 8.4 Hz, 1H), 6.85 (d, J=8.4 Hz, 1H), 6.76 (d, J=19.9 Hz, 1H), 4.81 (d, J=12.2 Hz, 2H), 4.72 (d, J=13.8 Hz, 2H), 3.85-3.83 (m, 4H), 3.12 (dd, J=8.8, 3.9 Hz, 4H), 2.33 (s, 2H), 1.28 (s, 6H). MS (ES) m/z 386.60 [M+1]$^+$.

Method E

Carbamates 5 were prepared according to Scheme 5. Carbonate 2 was prepared from alcohol 1 (US 2017/0029390 A1) and bis(pentafluorophenyl)carbonate in the presence of triethylamine. Coupling of 2 with amines 3 was accomplished as described in Method A to afford carbamates 4. Deprotection of 4 with catalytic hydrogenation (e.g., H$_2$, 10%, Pd/C) produced carbamates 5.

Scheme 5

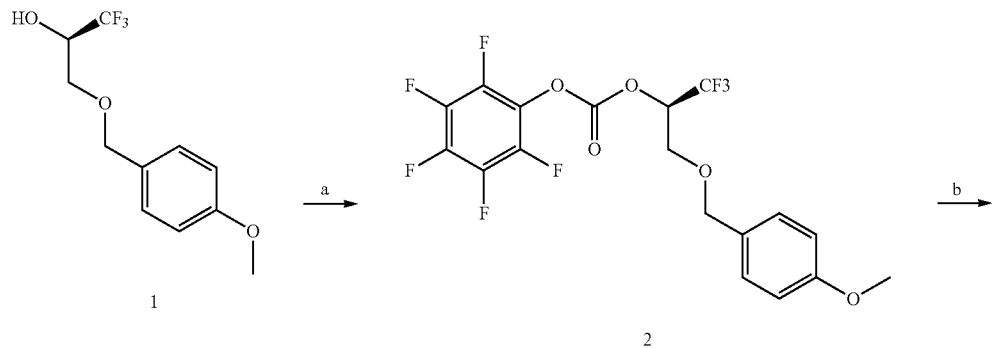

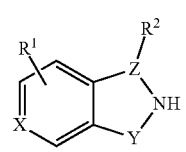

3
X = C, N
Y, Z = (CH$_2$)$_n$ n = 1-3
R$_1$, R$_2$ as defined above

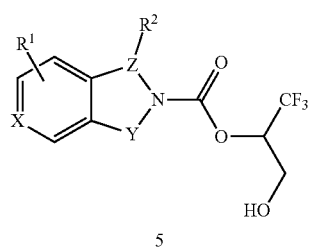 ← 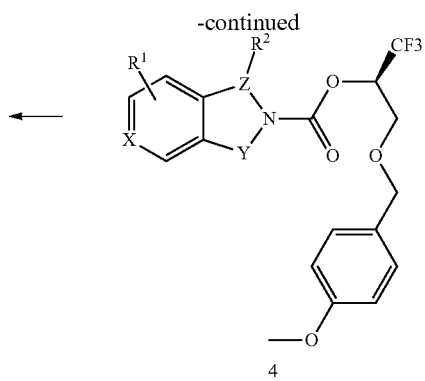

Reagents: (a) C₆F₅O)₂CO, Et₃N; (b) N,N-diisopropylethylamine, CHeCN; (c) 1,1,1,3,3,3-hexafluoropropan-2-ol, triphosgene, N,N-diisopropylethylamine, 0° C. to rt, 1 h; (d) 10% Pd/C, EtOAc The following examples were prepared according to Method E.

Example 40. (R)-1,1,1-trifluoro-3-hydroxypropan-2-yl 5-bromo-3,4-dihydroisoquinoline-2(1H)-carboxylate Step a). (R)-Perfluorophenyl (1,1,1-trifluoro-3-((4-methoxybenzyl)oxy)propan-2-yl) carbonate. This compound was synthesized according to the literature procedure as described in US 2017/0029390 A1.

Step b). (R)-1,1,1-trifluoro-3-((4-methoxybenzyl)oxy)propan-2-yl 5-bromo-3,4-dihydroisoquinoline-2(1H)-carboxylate. (R)-perfluorophenyl (1,1,1-trifluoro-3-((4-methoxybenzyl)oxy)propan-2-yl) carbonate (60 mg, 0.13 mmol) in acetonitrile (2 mL) was added into cold 0° C. solution of 5-bromo, 1,2,3,4-tetrahydroisoquinoline (30 mg, 0.14 mmol) and N,N-diisopropylethylamine (0.05 mL, 0.39 mmol) in acetonitrile (4 mL). The resulting reaction mixture was allowed to come to room temperature and stirred for 1 hour. Then, the reaction was diluted in dichloromethane (25 mL) and washed with water (2×15 mL). The organic extracts were dried over anhydrous NaSO₄. The solvents were removed under vacuum and the residue was purified on silica gel (Biotage; eluting solvents hexanes:EtOAc 4/1 ratio) to afford (R)-1,1,1-trifluoro-3-((4-methoxybenzyl)oxy)propan-2-yl 5-bromo-3,4-dihydroisoquinoline-2(1H)-carboxylate as colorless oil. ¹H NMR (400 MHz, CDCl₃) δ ppm 7.46-7.45 (m, 1H), 7.25-7.16 (m, 2H), 7.08-7.06 (m, 2H), 6.84-6.82 (m, 2H), 5.52-5.51 (sept, 1H), 4.64-4.61 (m, 2H), 4.52-4.44 (m, 2H), 3.78 (s, 3H), 3.76-3.71 (m, 3H), 2.90-2.87 (m, 2H).

Step c). (R)-1,1,1-trifluoro-3-hydroxypropan-2-yl 5-bromo-3,4-dihydroisoquinoline-2(1H)-carboxylate. 10% Pd/C (30 mg) was added into a stirred solution of (R)-1,1,1-trifluoro-3-((4-methoxybenzyl)oxy)propan-2-yl 5-bromo-3,4-dihydroisoquinoline-2(1H)-carboxylate (50 mg, 0.1 mmol) in ethyl acetate (10 mL). The resulting reaction mixture was stirred at room temperature in under a hydrogen atmosphere for 24 hours. Then, the mixture was filtered through celite pad. The filtrate was concentrated under reduced pressure and the residue was purified on silica gel (Biotage; eluting solvents hexanes:EtOAc 3/1 ratio) to afford 3-hydroxy-6,6-dimethyl-3-azabicyclo[3.1.0]hexane-2,4-dione as colorless oil (30 mg, 81% yield); ¹H NMR (400 MHz, CDCl₃) δ ppm 7.21-7.12 (m, 3H), 5.32-5.29 (sept, 1H), 4.66-4.65 (m, 2H), 4.04-4.00 (m, 1H), 3.92-3.87 (m, 1H), 3.75-3.72 (m, 2H), 2.89 (brs, 2H).

Method F

Carbamates 5 were prepared according to Scheme 6. Alkylation of 1 with an appropriately substituted alkyl halide or alkyl tosylate 2, as defined above, in the presence of an inorganic base (i.e. sodium hydride, cesium carbonate, etc.) in a polar aprotic solvent as N,N-dimethylformamide, dimethyl sulfoxide, etc. afforded 3. Deprotection of the BOC group of 3 and conversion to carbamates 5 was accomplished as described in Method C.

Scheme 6

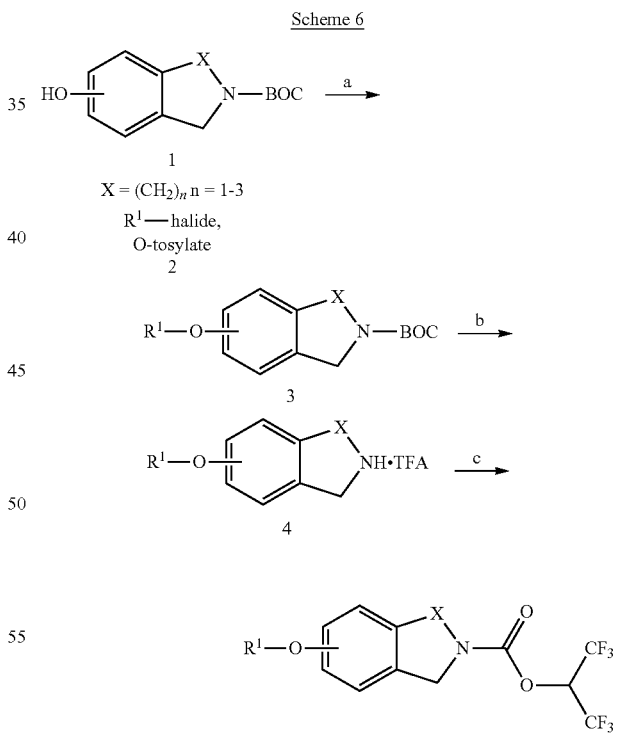

Reagents: (a) NaH, DMF, R¹- halide or R¹- tosylate; (b) (b) TFA, dichloromethane; (c) 1,1,1,3,3,3-hexafluoropropan-2-ol, triphosgene, N,N-diisopropylethylamine, 0° C. to rt, 1 h The following examples were prepared according to Method F

Example 41. 1,1,1,3,3,3-Hexafluoropropan-2-yl 5-(3-fluoropropoxy)-3,4-dihydroisoquinoline-2(1H)-carboxylate Step a). tert-Butyl 5-(3-fluoropropoxy)-3,4-dihydroisoquinoline-2(1H)-carboxylate. Sodium hydride (28.9 mg, 1.2 mmol) was added into a cold (° C.) solution of tert-butyl 3,4-dihydroisoquinoline-2(1H)-carboxylate (200 mg, 0.8 mmol) and DMF (3 mL). The reaction mixture was stirred for 1 hour and then, bromo-fluoropropane (226.2 mg, 1.6 mmol) was added. The reaction mixture was allowed to come to room temperature and stirred overnight. Then, the reaction mixture was quenched with aqueous ammonium chloride and extracted with ethyl acetate. The organic extracts were dried over anhydrous $MgSO_4$. The solvents were removed under vacuum and the residue was purified on silica gel (Biotage; eluting solvents hexanes:EtOAc 5/1 ratio) to afford tert-butyl 5-(3-fluoropropoxy)-3,4-dihydroisoquinoline-2(1H)-carboxylate as colorless oil (161.2 mg, 65% yield). $^1$H NMR (500 MHz, $CDCl_3$) δ ppm 7.15 (t, J=8 Hz, 1H), 6.72 (m, 2H), 4.72 (t, J=6 Hz, 1H), 4.62 (t, J=6 Hz, 1H), 4.56 (s, 2H), 4.11 (t, J=6.5 Hz, 2H), 3.64 (t, J=6 Hz, 2H), 2.76 (t, J=6 Hz, 2H), 2.23-2.20 (m, 1H), 2.17-2.15 (m, 1H), 1.48 (s, 9H).

Step b). 5-(3-Fluoropropoxy)-1,2,3,4-tetrahydroisoquinoline. TFA. The deprotection of the BOC group of tert-butyl 5-(3-fluoropropoxy)-3,4-dihydroisoquinoline-2(1H)-carboxylate was accomplished according to followed Method C. The crude trifluoroacetic salt 5-(3-fluoropropoxy)-1,2,3,4-tetrahydroisoquinoline. TFA was used to the next step without any further purification.

Step c). 1,1,1,3,3,3-Hexafluoropropan-2-yl 5-(3-fluoropropoxy)-3,4-dihydroisoquinoline-2(1H)-carboxylate. This step was performed according to Method A. $^1$H NMR (500 MHz, $CDCl_3$) δ ppm 7.21-7.16 (m, 1H), 6.76 (d, J=7.5 Hz, 2H), 5.82-5.79 (sept, 1H), 4.72 (t, J=6 Hz, 1H), 4.67 (s, 2H), 4.63 (t, J=6 Hz, 1H), 4.13 (dt, J=6, 2 Hz, 2H), 3.78 (dt, J=6, 4 Hz, 2H), 2.86-2.81 (m, 2H), 2.24-2.18 (m, 1H), 2.17-2.15 (m, 1H).

Example 42. 1,1,1,3,3,3-Hexafluoropropan-2-yl 5-(3-fluoropropoxy)isoindoline-2-carboxylate $^1$H NMR (500 MHz, $CDCl_3$) δ ppm 7.20 (q, J=8.5 Hz, 1H), 6.88 (d, J=9 Hz, 1H), 6.83 (d, J=16 Hz, 1H), 5.81-5.79 (sept, 1H), 4.79-4.75 (m, 4H), 4.71 (t, J=6 Hz, 1H), 4.62 (t, J=6 Hz, 1H), 4.11-4.08 (m, 2H), 2.22-2.19 (m, 1H), 2.17-2.15 (m, 1H).

Example 43. 1,1,1,3,3,3-Hexafluoropropan-2-yl 5-(cyclopropylmethoxy)isoindoline-2-carboxylate $^1$H NMR (500 MHz, $CDCl_3$) δ ppm 7.18 (q, J=8 Hz, 1H), 6.88 (dd, J=8.5, 2.5 Hz, 1H), 6.81 (d, J=12 Hz, 1H), 5.81-5.79 (sept, 1H), 4.78-4.74 (m, 4H), 3.81 (dd, J=4, 2.5 Hz, 2H), 1.27-1.26 (m, 1H), 0.67-0.65 (m, 2H), 0.37-0.35 (m, 2H).

Example 44. 1,1,1,3,3,3-Hexafluoropropan-2-yl 5-(2-morpholinoethoxy)isoindoline-2-carboxylate $^1$H NMR (500 MHz, $CDCl_3$) δ ppm 7.19 (q, J=8.5 Hz, 1H), 6.88 (dd, J=8.5 Hz, 1H), 6.83 (d, J=15 Hz, 1H), 5.81-5.78 (sept, 1H), 4.79-4.75 (m, 4H), 4.13-4.09 (m, 2H), 3.75-3.73 (m, 4H), 2.82 (t, J=5.5 Hz, 2H), 2.59 (d, J=4 Hz, 4H); MS (ES) m/z 443.56 [M+1]$^+$.

Example 45. 1,1,1,3,3,3-Hexafluoropropan-2-yl 5-(2,2-difluoroethoxy)isoindoline-2-carboxylate $^1$H NMR (500 MHz, $CDCl_3$) δ ppm 7.23 (q, J=8 Hz, 1H), 6.90 (dd, J=8.5, 2 Hz, 1H), 6.81 (d, J=14.5 Hz, 1H), 6.211 (tt, J=55, 55.5, 4 Hz, 1H), 5.81-5.79 (sept, 1H), 4.80-4.76 (m, 4H), 4.22-4.15 (tt, J=13.5, 13, 4 Hz, 2H).

Example 46. 1,1,1,3,3,3-Hexafluoropropan-2-yl 5-(2-(dimethylamino)ethoxy)isoindoline-2-carboxylate $^1$H NMR (500 MHz, $CDCl_3$) δ ppm 7.19 (q, J=8 Hz, 1H), 6.89 (dd, J=8, 2 Hz, 1H), 6.81 (dd, J=14, 2 Hz, 1H), 5.81-5.78 (sept, 1H), 4.76-4.75 (m, 4H), 4.13 (q, J=5 Hz, 2H), 2.88-2.83 (m, 2H), 2.44 (s, 6H). MS (ES) m/z 401.52 [M+1]$^+$.

Example 47. 1,1,1,3,3,3-Hexafluoropropan-2-yl 5-((2-morpholinoethyl)amino)isoindoline-2-carboxylate $^1$H NMR (500 MHz, $CDCl_3$) δ ppm 7.08 (q, J=8 Hz, 1H), 6.61-6.57 (m, 1H), 6.53 (d, J=18.5 Hz, 1H), 5.81-5.78 (sept, 1H), 4.74-4.70 (m, 4H), 3.73-3.71 (m, 4H), 3.16-3.148 (m, 2H), 2.65 (t, J=6 Hz, 2H), 2.48-2.43 (m, 4H). MS (ES) m/z 442.61 [M+1]$^+$.

Example 48. 1,1,1,3,3,3-Hexafluoropropan-2-yl 5-(2-(piperidin-1-yl)ethoxy)isoindoline-2-carboxylate $^1$H NMR (500 MHz, $CDCl_3$) δ ppm 7.14 (dd, J=16.8, 8.4 Hz, 1H), 6.85 (d, J=8.4 Hz, 1H), 6.79 (d, J=16.0 Hz, 1H), 5.78 (dt, J=12.3, 6.1 Hz, 1H), 4.74 (dd, J=12.2, 7.6 Hz, 4H), 4.08 (td, J=6.0, 2.7 Hz, 2H), 2.76 (t, J=6.0 Hz, 2H), 2.49 (s, 4H), 1.61-1.58 (m, 4H), 1.44 (d, J=5.0 Hz, 2H). MS (ES) m/z 441.60 [M+1]$^+$.

Example 49. 1,1,1,3,3,3-Hexafluoropropan-2-yl 5-(2-(pyrrolidin-1-yl)ethoxy)isoindoline-2-carboxylate $^1$H NMR (500 MHz, $CDCl_3$) δ ppm 7.14 (dd, J=16.7, 8.4 Hz, 1H), 6.83 (dd, J=32.1, 11.2 Hz, 2H), 5.78 (dt, J=12.4, 6.2 Hz, 1H), 4.75 (dd, J=12.8, 7.8 Hz, 4H), 4.08 (dd, J=9.4, 5.8 Hz, 2H), 2.89 (t, J=5.9 Hz, 2H), 2.61 (s, 4H), 1.80 (s, 4H). MS (ES) m/z 421.61 [M+1]$^+$.

Example 50. 1,1,1,3,3,3-Hexafluoropropan-2-yl 5-(2-morpholino-2-oxoethoxy)isoindoline-2-carboxylate $^1$H NMR (500 MHz, $CDCl_3$) δ ppm 7.17 (dd, J=15.3, 8.4 Hz, 1H), 6.89 (d, J=8.4 Hz, 1H), 6.84 (d, J=11.1 Hz, 1H), 5.77 (dt, J=12.4, 6.2 Hz, 1H), 4.75 (dd, J=14.7, 9.4 Hz, 4H), 4.69 (d, J=2.5 Hz, 2H), 3.68-3.63 (m, 4H), 3.60 (dd, J=15.6, 4.0 Hz, 4H). MS (ES) m/z 457.54 [M+1]$^+$.

Example 51. 1,1,1,3,3,3-Hexafluoro-2-methylpropan-2-yl 5-(2-morpholinoethoxy)isoindoline-2-carboxylate $^1$H NMR (500 MHz, $CDCl_3$) δ ppm 7.15 (dd, J=16.3, 8.4 Hz, 1H), 6.85 (d, J=8.5 Hz, 1H), 6.79 (d, J=13.9 Hz, 1H), 4.68 (dd, J=13.1, 7.9 Hz, 4H), 4.10 (td, J=5.6, 2.4 Hz, 2H), 3.74-3.73 (m, 4H), 2.80 (t, J=5.7 Hz, 2H), 2.58 (s, 4H), 2.05 (s, 3H). MS (ES) m/z 457.60 [M+1]+.

Method G

Spiro-type carbamates 5 were prepared according to Scheme 7. The Mitsunobu protocol (PPh₃/diisopropyl azodicarboxylate) was applied to couple alcohols 2 with phenols 1 to generate adducts 3. Deprotection of the BOC group and conversion to carbamates 5 was accomplished as described in Method C.

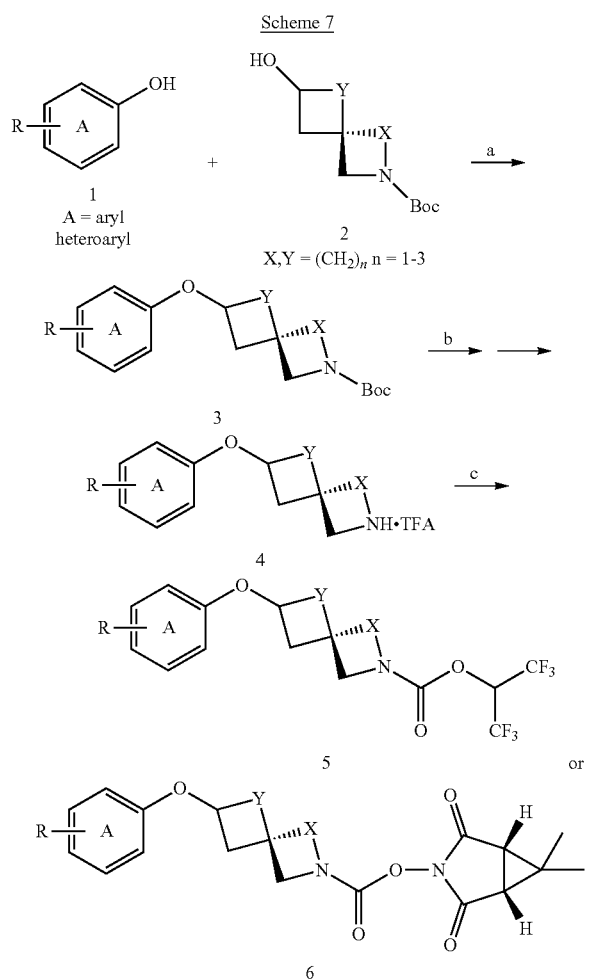

Scheme 7

Reagents: (a) 3-(trifluoromethyl)phenol, tert-butyl 6-hydroxy-2-azaspiro[3.3]heptane-2-carboxylate, PPh₃, diisopropyl azodicarboxylate; (b) trifluoroacetic acid, dichloromethane; (c) hexafluoroisopropanol, triphosgene, N,N-diisopropylethylamine, 0° C. to rt, 1 h or 3-hydroxy-6,6-dimethyl-3-azabicyclo[3.1.0]hexane-2,4-dione, triphosgene, N,N-diisopropylethylamine, 0° C. to rt, 1 h The following examples were prepared according to Method G.

Example 52. 1,1,1,3,3,3-Hexafluoropropan-2-yl 6-(3-(trifluoromethyl)phenoxy)-2-azaspiro [3.3]heptane-2-carboxylate Step a). tert-butyl 6-(3-(trifluoromethyl)phenoxy)-2-azaspiro[3.3]heptane-2-carboxylate. Diisopropyl azodicarboxylate (4.04 g, 20 mmol) was added into a cold (0° C.) solution of (3-trifluoromethyl)phenol (1.62 g, 10 mmol)), tert-butyl 6-hydroxy-2-azaspiro[3.3]heptane-2-carboxylate (2.34 g, 11 mmol) and triphenylphosphine (5.24 g, 20 mmol) in anhydrous benzene (20 mL) The resulting mixture was refluxed overnight. Then, the mixture was concentrated and partitioned between EtOAc and water (1/1). The organic layer was washed with saturated NaHCO₃ and brine. The organic extracts were dried over anhydrous NaSO₄. The solvents were removed under vacuum and the residue was purified on silica gel (Biotage; eluting solvents hexanes: EtOAc 3/1 ratio) to afford tert-butyl 6-(3-(trifluoromethyl)phenoxy)-2-azaspiro[3.3]heptane-2-carboxylate as colorless oil (1.4 g, 40% yield); ¹H NMR (400 MHz, CDCl₃) δ ppm 7.36-7.34 (m, 1H), 7.20-7.18 (m, 1H), 6.99 (s, 1H), 6.95-6.92 (m, 1H), 4.61-4.57 (m, 1H), 3.99 (s, 2H), 3.93 (s, 2H), 2.75-2.70 (m, 2H), 2.37-2.32 (m, 2H), 1.43 (s, 9H).

Step b). 6-(3-(Trifluoromethyl)phenoxy)-2-azaspiro[3.3] heptane.TFA. The deprotection of the BOC group of tert-butyl 6-(3-(trifluoromethyl)phenoxy)-2-azaspiro[3.3]heptane-2-carboxylate followed Method C. The crude trifluoroacetic salt 6-(3-(trifluoromethyl)phenoxy)-2-azaspiro[3.3]heptane.TFA was used to the next step without any further purification.

Step c). 1,1,1,3,3,3-hexafluoropropan-2-yl 6-(3-(trifluoromethyl)phenoxy)-2-azaspiro[3.3] heptane-2-carboxylate. This step was performed according to Method A to afford 1,1,1,3,3,3-hexafluoropropan-2-yl 6-(3-(trifluoromethyl)phenoxy)-2-azaspiro[3.3] heptane-2-carboxylate. ¹H NMR (400 MHz, CDCl₃) δ ppm 7.39-7.35 (m, 1H), 7.25-7.20 (m, 1H), 6.99-6.92 (m, 2H), 5.67-5.61 (sept, 1H), 4.64-4.60 (m, 1H), 4.20-4.11 (m, 4H), 2.82-2.77 (m, 2H), 2.42 (brs, 2H).

Example 53. 1,1,1,3,3,3-Hexafluoropropan-2-yl-6-(3-fluorophenoxy)-2-azaspiro[3.3]heptane-2-carboxylate ¹H NMR (500 MHz, CDCl₃) δ ppm 7.23-7.19 (m, 1H), 6.67 (dt, J=8.5, 2 Hz, 1H), 6.57 (dd, J=8.5, 2 Hz, 1H), 6.50 (d, J=11 Hz, 1H), 5.65-5.63 (sept, 1H), 4.60-4.52 (m, 1H), 4.19 (dd, J=19, 15 Hz, 4H), 2.80-2.75 (m, 2H), 2.42-2.39 (m, 2H).

Example 54. 1,1,1,3,3,3-Hexafluoropropan-2-yl-6-(3-methoxyphenoxy)-2-azaspiro[3.3]heptane-2-carboxylate ¹H NMR (500 MHz, CDCl₃) δ ppm 7.18 (t, J=8 Hz, 1H), 6.53 (dd, J=2.5, 8.5 Hz, 1H), 6.37-6.34 (m, 2H), 5.64-5.63 (sept, 1H), 4.59-4.51 (m, 1H), 4.18-4.10 (m, 4H), 3.78 (s, 3H), 2.78-2.74 (m, 2H), 2.45-2.34 (m, 2H).

Example 55. 1,1,1,3,3,3-Hexafluoropropan-2-yl-6-(3-phenoxyphenoxy)-2-azaspiro[3.3]heptane-2-carboxylate ¹H NMR (500 MHz, CDCl₃) δ ppm 7.36-7.33 (m, 2H), 7.21 (t, J=8.5 Hz, 1H), 7.13 (t, J=8.5 Hz, 1H), 7.02 (d, J=8.5 Hz, 2H), 6.60 (dd, J=2.5, 8.5 Hz, 1H), 6.51 (d, J=8.5 Hz, 1H), 6.42 (d, J=2 Hz, 1H), 5.66-5.61 (sept, 1H), 4.58-4.48 (m, 1H), 4.16-4.09 (m, 4H), 2.75-2.71 (m, 2H), 2.44-2.32 (m, 2H).

Example 56. 1,1,1,3,3,3-Hexafluoropropan-2-yl 6-(3-(trifluoromethoxy)phenoxy)-2-azaspiro[3.3] heptane-2-carboxylate ¹H NMR (500 MHz, CDCl₃) δ ppm 7.29-7.26 (m, 1H), 6.83 (d, J=8.5 Hz, 1H), 6.71 (dd, J=8, 1.5 Hz, 1H), 6.63 (s, 1H), 5.67-5.62 (sept, 1H), 4.61-4.56 (m, 1H), 4.20 (dd, J=21, 17 Hz, 4H) 2.81-2.77 (m, 2H), 2.43-2.40 (m, 2H).

Example 57. 1,1,1,3,3,3-Hexafluoropropan-2-yl 2-(3-fluorophenoxy)-6-azaspiro[3.4]octane-6-carboxylate ¹H NMR (400 MHz, CDCl₃) δ ppm 7.29-7.23 (m, 1H), 6.69-6.50 (m, 3H), 5.78-5.75 (m, 1H), 4.72-4.69 (m, 1H), 3.55-3.42 (m, 4H), 2.60-2.58 (m, 2H), 2.25-2.15 (m, 2H) 2.07-2.05 (m, 2H).

Example 58. 1,1,1,3,3,3-Hexafluoropropan-2-yl 2-(3-fluorophenoxy)-6-azaspiro[3.4]octane-6-carboxylate ¹H NMR (400 MHz, CDCl₃) δ ppm 7.22-7.19 (m, 1H), 6.68-6.49 (m, 3H), 5.74-5.70 (m, 1H), 4.71-4.64 (m, 1H), 3.57 (t, J=7 Hz, 2H), 3.46 (d, J=5 Hz, 2H), 2.55-2.50 (m, 2H), 2.29-2.22 (m, 2H) 2.04-1.98 (m, 2H).

Example 59. 1,1,1,3,3,3-Hexafluoropropan-2-yl 6-(3-fluorophenoxy)-2-azaspiro[3.4]octane-2-carboxylate ¹H NMR (500 MHz, CDCl₃) δ ppm 7.23 (q, J=8 Hz, 1H), 6.66-6.60 (m, 2H), 6.54 (d, J=11 Hz, 1H), 5.68-5.63 (m, 1H), 4.79-4.77 (m, 1H), 4.12-4.07 (m, 1H), 4.03-3.96 (m, 3H), 2.27 (d, J=15 Hz, 1H), 2.19-2.04 (m, 3H), 1.97-1.90 (m, 2H).

Example 60. 1,1,1,3,3,3-Hexafluoropropan-2-yl 6-((5-fluoropyridin-3-yl)oxy)-2-azaspiro[3.3]heptane-2-carboxylate ¹H NMR (500 MHz, CDCl₃) δ ppm 8.11 (s, 1H), 8.02 (s, 1H), 6.82 (d, J=9.5 Hz, 1H), 5.66-5.60 (m, 1H), 4.63-4.60 (m, 1H), 4.19 (dd, J=17.5, 7.5 Hz, 4H), 2.82-2.78 (m, 2H), 2.48-2.39 (m, 2H). MS (ES) m/z 403.49 [M+1]⁺

Example 61. 1,1,1,3,3,3-Hexafluoropropan-2-yl 6-((5-fluoropyridin-3-yl)oxy)-2-azaspiro[3.4]octane-2-carboxylate ¹H NMR (500 MHz, CDCl₃) δ ppm 8.11 (d, J=16 Hz, 2H), 6.89 (d, J=10 Hz, 1H), 5.68-5.63 (m, 1H), 4.84-4.82 (m, 1H), 4.13-3.98 (m, 4H), 2.29-1.94 (m, 6H). MS (ES) m/z 417.53 [M+1]⁺.

Example 62. 1,1,1,3,3,3-Hexafluoropropan-2-yl 6-(benzo[d]isoxazol-6-yloxy)-2-azaspiro[3.3]heptane-2-carboxylate ¹H NMR (500 MHz, CDCl₃) δ ppm 7.42 (d, J=8.5 Hz, 1H), 6.46 (dd, J=8.5, 2.1 Hz, 1H), 6.23 (s, 1H), 6.09 (s, 1H), 5.63 (s, 1H), 4.63 (d, J=6.9 Hz, 1H), 4.22-4.08 (m, 4H), 2.84-2.74 (m, 2H), 2.51 (s, 2H).

Example 63. 6,6-Dimethyl-2,4-dioxo-3-azabicyclo[3.1.0]hexan-3-yl 6-(3-(trifluoromethyl)phenoxy)-2-azaspiro[3.3]heptane-2-carboxylate Step a) Imide carbamates were synthesized according to Method D step c). 6,6-Dimethyl-2,4-dioxo-3-azabicyclo[3.1.0]hexan-3-yl 6-(3-(trifluoromethyl)phenoxy)-2-azaspiro[3.3]heptane-2-carboxylate: ¹H NMR (500 MHz, CDCl₃) δ ppm 7.39-7.38 (m, 1H), 7.21 (d, J=8 Hz, 1H), 6.98 (s, 1H), 6.93 (d, J=8 Hz, 1H), 4.63-4.60 (m, 1H), 4.29-4.25 (m, 2H), 4.16-4.12 (m, 2H), 2.81-2.77 (m, 2H), 2.43-2.39 (m, 2H), 2.32 (s, 2H), 1.28 (s, 6H).

Example 64. 6,6-Dimethyl-2,4-dioxo-3-azabicyclo[3.1.0]hexan-3-yl 6-((5-fluoropyridin-3-yl)oxy)-2-azaspiro[3.4]octane-2-carboxylate ¹H NMR (400 MHz, CDCl₃) δ ppm 8.09-8.05 (m, 2H), 6.87-6.84 (m, 1H), 4.82-4.79 (m, 1H), 4.19-4.00 (m, 4H), 2.30 (s, 2H), 2.20-2.09 (m, 4H), 1.97-1.91 (m, 2H), 1.27 (s, 6H). MS (ES) m/z 404.55 [M+1]⁺

Method H

Spiro-type carbamates 5 were prepared according to Scheme 8. Palladium catalyzed coupling of aryl halides or O-triflates 1 and amines 2 afforded adducts 3. Deprotection of the BOC group of 3 and conversion to carbamates 5 was accomplished as described in Method C.

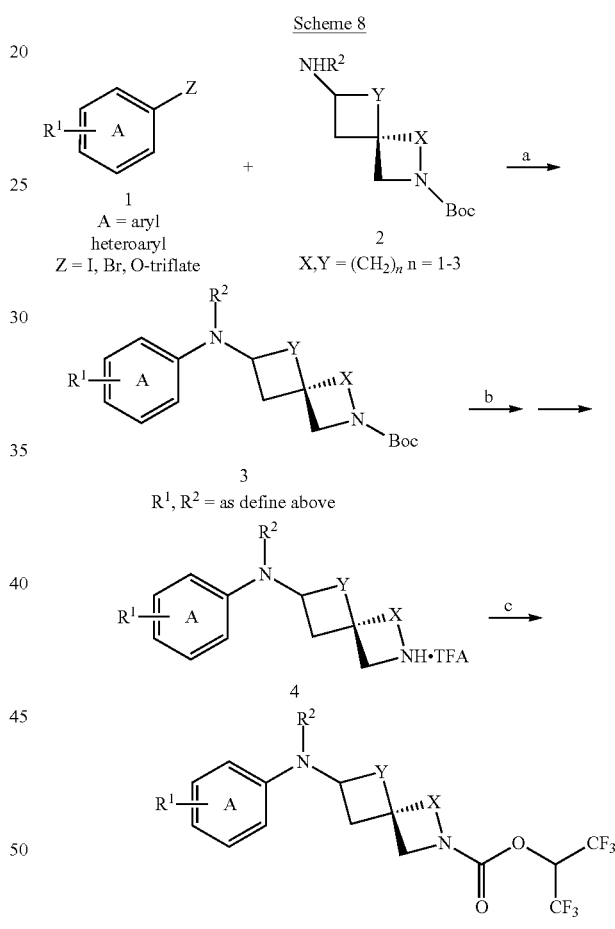

Scheme 8

Reagents: (a) Tris(dibenzylideneacetone)dipalladium(0), 2-(di-tert-butylphosphino) biphenyl, sodium tert-butoxide; (b) trifluoroacetic acid, dichloromethane; (c) hexafluoroisopropanol, triphosgene, N,N-diisopropylethylamine, 0° C. to rt, 1 h The following example was prepared according to Method H

Example 65. 1,1,1,3,3,3-Hexafluoropropan-2-yl 6-((3-(trifluoromethyl)phenyl)amino)-2-azaspiro[3.3]heptane-2-carboxylate Step a). tert-Butyl 6-((3-(trifluoromethyl)phenyl)amino)-2-azaspiro[3.3]heptane-2-carboxylate. Tris(dibenzylideneacetone)dipalladium(0) (71.88 mg, 0.08 mmol), 2-(di-tert-butylphosphino) biphenyl (23.4 mg, 0.08 mmol) and sodium tert-butoxide (113.16 mg, 1.18 mmol) were added into a solution of tert-butyl 6-amino 2-azaspiro [3.3]heptane 2-carboxylate (200 mg, 0.94 mmol) in toluene (2.5 mL). The reaction mixture was purged with argon for 5 minutes and then 1-iodo 3-(trifluoromethyl)benzene (113 μL, 0.79 mmol) was added and the mixture and stirred at 80° C. for 2 hours. After the completion of the reaction (monitored by TLC) the solvent was removed under vacuum, ethyl acetate was added and washed with water three times. The organic layer was dried over $Na_2SO_4$. The solvents were removed under vacuum and the residue was purified on silica gel (Biotage; eluting solvents hexane:EtOAc 4:1 ratio) to afford tert-butyl 6-((3-(trifluoromethyl)phenyl)amino)-2-azaspiro[3.3]heptane-2-carboxylate as brown solid (315 mg, 112% yield); $^1$H NMR (400 MHz, CDCl$_3$) δ ppm 7.26 (t, J=8 Hz, 1H), 6.95 (d, J=7.6 Hz, 1H), 6.69 (s, 1H), 6.66 (d, J=8 Hz, 1H), 4.00 (s, 2H), 3.94 (m, 1H), 3.89 (s, 2H), 3.86-3.81 (m, 1H), 2.72-2.67 (m, 2H), 2.05-2.02 (m, 2'H), 1.44 (s, 9H).

Step b). N-(3-(trifluoromethyl)phenyl)-2-azaspiro[3.3] heptan-6-amine.TFA. The deprotection of the BOC group of The deprotection of the BOC group of tert-butyl 5-(3-fluoropropoxy)-3,4-dihydroisoquinoline-2(1H)-carboxylate followed Method Z. The crude trifluoroacetic salt N-(3-(trifluoromethyl)phenyl)-2-azaspiro[3.3]heptan-6-amine.TFA was used to the next step without any further purification.

Step c). 1,1,1,3,3,3-Hexafluoropropan-2-yl 6-((3-(trifluoromethyl)phenyl)amino)-2-azaspiro[3.3]heptane-2-carboxylate. This step was performed according to Method C. $^1$H NMR (500 MHz, CDCl$_3$) δ ppm 7.27-7.24 (m, 1H), 6.97 (d, J=7.5 Hz, 1H), 6.70 (s, 1H), 6.66 (d, J=8 Hz, 1H), 5.66-5.63 (sept, 1H), 4.22 (d, J=27 Hz, 2H), 4.12 (d, J=25 Hz, 2H), 3.86-3.83 (m, 1H), 2.79-2.75 (m, 2H), 2.08-2.11 (m, 2H).

Example 66. 1,1,1,3,3,3-Hexafluoropropan-2-yl 6-((3-methoxyphenyl)amino)-2-azaspiro[3.3]heptane-2-carboxylate $^1$H NMR (500 MHz, CDCl$_3$) δ ppm 7.10 (t, J=8 Hz, 1H), 6.31 (dd, J=8, 2 Hz, 1H), 6.16 (d, J=8 Hz, 1H), 6.06 (s, 1H), 5.66-5.63 (sept, 1H), 4.20 (q, J=25 Hz, 4H), 3.84-3.77 (m, 1H), 3.77 (s, 3H), 2.75-2.71 (m, 2H), 2.09-2.04 (m, 2H). MS (ES) m/z 413.56 [M+1]$^+$.
Method I Step a). tert-Butyl 2-(bis(4-fluorophenyl)methoxy)-6-azaspiro[3.4]octane-6-carboxylate. Sodium hydride (28.9 mg, 1.2 mmol) was added into a cold (0° C.) solution of tert-butyl 2-hydroxy-6-azaspiro[3.4]octane-6-carboxylate (227 mg, 1 mmol) and DMF (5 mL). The reaction mixture was stirred for 1 hour and then, 4,4'-(chloromethylene)bis (fluorobenzene) (285.6 mg, 1.2 mmol) was added. The resulting mixture was heated at 80° C. overnight. The reaction mixture was allowed to come to room temperature and the reaction mixture was quenched with aqueous ammonium chloride and extracted with ethyl acetate. The organic extracts were dried over anhydrous MgSO$_4$. The solvents were removed under vacuum and the residue was purified on silica gel (Biotage; eluting solvents hexanes:EtOAc 9/1 ratio) to afford tert-butyl 2-(bis(4-fluorophenyl)methoxy)-6-azaspiro[3.4]octane-6-carboxylate as colorless oil (250 mg, 58% yield). $^1$H NMR (500 MHz, CDCl$_3$) δ ppm 7.27-7.24 (m, 4H), 7.02-6.99 (m, 4H), 5.28 (s, 1H), 3.99-3.96 (m, 1H), 3.32-3.21 (m, 4H), 2.22-2.14 (m, 2H), 2.04-1.96 (m, 2H), 1.83 (t, J=6.5 Hz, 1H), 1.73 (d, J=5.6 Hz, 1H), 1.44 (d, J=2.7 Hz, 9H).

Step b). 2-(Bis(4-fluorophenyl)methoxy)-6-azaspiro[3.4] octane.TFA. Trifluoroacetic acid (80 mg, 0.69 mmol) was slowly added into a cold (0° C.) solution of tert-butyl 2-(bis(4-fluorophenyl)methoxy)-6-azaspiro[3.4]octane-6-carboxylate (250 mg, 0.58 mmol) and dichloromethane (10 mL). The resulting reaction mixture was stirred at room temperature for 2 hours. Then, the mixture was concentrated under vacuum and CHCl$_3$ (2×15 mL) was added and evaporated to ensure removal of the trifluoroacetic acid. The product 2-(bis(4-fluorophenyl)methoxy)-6-azaspiro[3.4]octane.TFA was used in the next step without any further purification.

Step c). 1,1,1,3,3,3-hexafluoropropan-2-yl (2r,4s)-2-(bis (4-fluorophenyl)methoxy)-6-azaspiro[3.4]octane-6-carboxylate and 1,1,1,3,3,3-hexafluoropropan-2-yl (2s,4r)-2-(bis(4-fluorophenyl)methoxy)-6-azaspiro[3.4]octane-6-carboxylate. Triphosgene (115 mg, 0.388 mmol) was added into a cold (0° C.) solution of 1,1,1,3,3,3-hexafluoropropan-2-ol (198 mg, 1.180 mmol), N,N-diisopropylethylamine (0.3 mL, 2.35 mmol) and dichloromethane (5 mL). The reaction mixture was allowed to come to room temperature and stirred for 30 minutes. The resulting solution was added dropwise into cold (0° C.) solution of 2-(bis(4-fluorophenyl) methoxy)-6-azaspiro[3.4]octane.TFA (265 mg, 0.590 mmol) and N,N-diisopropylethylamine (0.08 mL, 0.590 mmol) in dichloromethane (5 mL). The reaction mixture was allowed to come to room temperature and stirred for 1 hour. Then, the reaction was diluted in dichloromethane (25 mL) and washed with water (2×15 mL) and brine. The organic extracts were dried over anhydrous Na$_2$SO$_4$. The solvents were removed under vacuum and the residue was purified on silica gel (Biotage; eluting solvents hexanes:EtOAc 19/1 ratio)) to afford 1,1,1,3,3,3-hexafluoropropan-2-yl (2r,4s)-2-(bis(4-fluorophenyl)methoxy)-6-azaspiro[3.4]octane-6-carboxylate and 1,1,1,3,3,3-hexafluoropropan-2-yl (2s,4r)-2-(bis(4-fluorophenyl)methoxy)-6-azaspiro[3.4]octane-6-carboxylate in 30% yield.

Example 67. 1,1,1,3,3,3-Hexafluoropropan-2-yl (2r, 4s)-2-(bis(4-fluorophenyl)methoxy)-6-azaspiro[3.4] octane-6-carboxylate $^1$H NMR (500 MHz, CDCl$_3$) δ ppm 7.26 (t, J=6.8 Hz, 4H), 7.01 (t, J=8.6 Hz, 4H), 5.79-5.62 (m, 1H), 5.28 (s, 1H), 4.01 (td, J=7.1, 3.7 Hz, 1H), 3.45 (t, J=6.9 Hz, 2H), 3.40 (s, 2H), 2.22-2.17 (m, 2H), 2.11-2.05 (m, 2H), 1.85-1.80 (m, 2H).

Example 68. 1,1,1,3,3,3-Hexafluoropropan-2-yl (2s, 4r)-2-(bis(4-fluorophenyl)methoxy)-6-azaspiro[3.4] octane-6-carboxylate $^1$H NMR (500 MHz, CDCl$_3$) δ ppm 7.28-7.24 (m, 4H), 7.01 (td, J=8.6, 1.8 Hz, 4H), 5.70 (d, J=5.6 Hz, 1H), 5.28 (d, J=3.6 Hz, 1H), 4.02-3.98 (m, 1H), 3.43 (t, J=6.9 Hz, 2H), 3.33 (d, J=5.1 Hz, 2H), 2.25-2.21 (m, 2H), 2.07-2.01 (m, 2H), 1.96-1.91 (m, 2H).

The following example were prepared according to Method I.

Example 69. 1,1,1,3,3,3-Hexafluoropropan-2-yl 6-(bis(4-fluorophenyl)methoxy)-2-azaspiro[3.4]octane-2-carboxylate $^1$H NMR (500 MHz, CDCl$_3$) δ ppm 7.26-7.21 (m, 4H), 7.03-6.99 (m, 4H), 5.65 (dt, J=12.0, 5.8 Hz, 1H), 5.32 (s, 1H), 4.06 (d, J=8.9 Hz, 1H), 3.94 (dd, J=22.7, 14.6 Hz, 4H), 2.10-2.08 (m, 2H), 1.98-1.91 (m, 1H), 1.86-1.79 (m, 3H).

Example 70. 1,1,1,3,3,3-Hexafluoropropan-2-yl 6-(bis(4-fluorophenyl)methoxy)-2-azaspiro[3.3]heptane-2-carboxylate $^1$H NMR (500 MHz, CDCl$_3$) δ ppm 7.29-7.19 (m, 4H), 7.03-6.99 (m, J=8.6 Hz, 4H), 5.61 (dt, J=12.5, 6.2 Hz, 1H), 5.26 (s, 1H), 4.02 (dd, J=19.7, 13.6 Hz, 4H), 3.91-3.85 (m, 1H), 2.44 (s, 2H), 2.21 (s, 2H).

Example 71. 1,1,1,3,3,3-Hexafluoropropan-2-yl 2-(benzyloxy)-6-azaspiro[3.4]octane-6-carboxylate $^1$H NMR (500 MHz, CDCl$_3$) δ ppm 7.37-7.29 (m, 5H), 5.72 (dt, J=6.3, 4.9 Hz, 1H), 4.42 (d, J=1.7 Hz, 2H), 4.10-4.06 (m, 1H), 3.49-3.44 (m, 2H), 3.41-3.38 (m, 2H), 2.34-2.25 (m, 2H), 2.10-2.01 (m, 2H), 1.97-1.86 (m, 2H).
Method J Example 72. 1,1,1,3,3,3-Hexafluoropropan-2-yl (2s,4r)-2-((bis(4-fluorophenyl)methyl)amino)-6-azaspiro[3.4]octane-6-carboxylate Step a). tert-Butyl 2-((bis(4-fluorophenyl)methyl)amino)-6-azaspiro[3.4]octane-6-carboxylate. Sodium triacetoxyborohydride (211 mg, 1 mmol), was added to a stirred solution of tert-butyl 2-oxo-6-azaspiro[3.4]octane-6-carboxylate (112 mg, 0.5 mmol), bis(4-fluorophenyl)methanamine hydrochloride (128 mg, 0.5 mmol) and acetic acid (45 mg, 0.75 mmol) in MeOH (15 mL) under an argon atmosphere. The resulting mixture was stirred at room temperature for 18 h and was then concentrated under reduced pressure. The residue was partitioned between saturated aqueous sodium bicarbonate and ethyl acetate. The organic extracts were dried over anhydrous MgSO$_4$. The solvents were removed under vacuum and the residue was purified on silica gel (Biotage; eluting solvents hexanes:EtOAc 4/1 ratio) to afford tert-butyl 2-((bis(4-fluorophenyl)methyl)amino)-6-azaspiro[3.4]octane-6-carboxylate as colorless oil (128 mg, 60%). $^1$H NMR (500 MHz, CDCl$_3$) δ ppm 7.31 (dd, J=8.3, 5.5 Hz, 4H), 6.98 (t, J=8.6 Hz, 4H), 4.75 (s, 1H), 3.32-3.13 (m, 5H), 2.12-2.16 (m, 2H), 1.76-1.72 (m, 2H), 1.65 (s, 2H), 1.44 (s, 9H).

Step b). N-(bis(4-fluorophenyl)methyl)-6-azaspiro[3.4]octan-2-amine.TFA. Trifluoroacetic acid (0.1 mL, 1.28 mmol) was slowly added into a cold (0° C.) solution of tert-butyl 2-((bis(4-fluorophenyl)methyl)amino)-6-azaspiro[3.4]octane-6-carboxylate (110 mg, 0.25 mmol) and dichloromethane (5 mL). The resulting reaction mixture was stirred at room temperature for 6 hours. Then, the mixture was concentrated under vacuum and CHCl$_3$ (2×15 mL) was added and evaporated to ensure removal of the trifluoroacetic acid. The product 2-(bis(4-fluorophenyl)methoxy)-6-azaspiro[3.4]octane.TFA was used in the next step without any further purification.

Step c). 1,1,1,3,3,3-hexafluoropropan-2-yl (2s,4r)-2-((bis(4-fluorophenyl)methyl)amino)-6-azaspiro[3.4]octane-6-carboxylate. This step was performed according to Method H, step C. $^1$H NMR (500 MHz, CDCl$_3$) δ ppm 7.32-7.29 (m, 4H), 7.00-6.95 (m, 4H), 5.72-5.66 (m, 1H), 4.75 (s, 1H), 3.45-3.42 (m, 2H), 3.34 (s, 2H), 3.19-3.17 (m, 1H), 2.23-2.17 (m, 2H), 1.86-1.75 (m, 4H).

Example 73. 1,1,1,3,3,3-Hexafluoropropan-2-yl 6-((5-methoxypyridin-3-yl)amino)-2-azaspiro[3.3]heptane-2-carboxylate $^1$H NMR (500 MHz, CDCl$_3$) δ ppm 7.72 (d, J=2.5 Hz, 1H), 7.60 (s, 1H), 6.30 (s, 1H), 5.66-5.61 (m, 1H), 4.20-4.12 (m, 4H), 3.82 (s, 3H), 3.81-3.80 (m, 1H), 2.77-2.73 (m, 2H), 2.10 (s, 2H).

Example 74. 1,1,1,3,3,3-Hexafluoropropan-2-yl 6-((5-fluoropyridin-3-yl)amino)-2-azaspiro[3.3]heptane-2-carboxylate $^1$H NMR (500 MHz, CDCl$_3$) δ ppm 7.83 (d, J=3 Hz, 1H), 7.76 (s, 1H), 6.48 (d, J=10.8 Hz, 1H), 5.65-5.62 (m, 1H), 4.21-4.06 (m, 4H), 3.80-3.79 (m, 1H), 2.79-2.74 (m, 2H), 2.13-2.09 (m, 2H).
Evaluation of ABHD6, MGL and FAAH Inhibition of Test Compounds Certain compounds were tested for their ABHD6 and dual ABHD6/MGL inhibitory activity, which is expressed as % of inhibition or IC$_{50}$ values in Table 1. The percentage of inhibition describes the percentage by which the inhibitor reduces the velocity/rate of 2-AG hydrolysis by ABHD6, and MGL or AEA hydrolysis by FAAH. The IC$_{50}$ is the concentration of the inhibitor, which results in 50% inhibition of the velocity/rate of 2-AG hydrolysis by ABHD6 or MGL. The IC$_{50}$ is the concentration of the inhibitor, which results in 50% inhibition of the velocity/rate of AEA hydrolysis by FAAH. The lower the IC$_{50}$ values, the higher its inhibitory activity. A detailed description of the methods used to test inhibitory activity of compounds is given below.

Example 75. Preparation of Human MAGL (hMAGL)

Recombinant hexahistidine-tagged human MAGL (hMAGL) was expressed in *E. coli* cells and purified following our recently reported procedures (Zvonok et al *Chem. Biol.* (2008) 15: 854-862), (Zvonok et al *J Proteome Res.* (2008) 7: 2158-2164).

Example 76. Preparation of Rat MGL (rMGL)

Recombinant rMAGL (rMAGL) was expressed in *E. coli* cells and purified as described for Hmag, (Zvonok et al *Chem. Biol.* (2008) 15: 854-862), (Zvonok et al *J Proteome Res.* (2008) 7: 2158-2164).

Example 77. Fluorescent Assay Protocol for hMGL

Compound inhibition of hMGL activity was assessed by a fluorometric assay recently developed in our laboratory (Makriyannis et al WO Patent Application 2009/117444 A1, (2009) 109 pp.), (Zvonok et al *Chem. Biol.* (2008) 15: 854-862), (Zvonok et al *J. Proteome Res.* (2008) 7: 158-2164). This medium throughput assay involved a 96-well plate format in which hMGL activity was monitored by the hydrolysis of the substrate 7-hydroxy-6-methoxy-4-methylcoumarin ester (AHMMCE) to form the fluorescent product, coumarin. In brief, various concentrations of each compound were preincubated with hMGL (175 ng of total protein in *E. coli* lysate containing hMGL) for 15 min at room temperature. Upon the addition of AHMMCE, the reaction was incubated at 25° C. for 120 min; fluorescence readings were taken every 15 min at 360 nm/460 nm (λexcitation/λemission) using a Synergy HT Plate Reader (Bio-Tek, Winooski, Vt.). Under these incubation conditions, negligible spontaneous AHMMCE hydrolysis was observed. External standards were used to convert relative fluorescence units to the amount of 4-methylcoumarin formed. All MGL assays were performed in triplicate for each inhibitor concentration, and IC50 values were calculated using Prizm software (GraphPad Software, Inc., San Diego, Calif.).

Example 78. Fluorescent Assay Protocol for rMAGL

Procedure was followed as described for hMAGL (Makriyannis et al WO Patent Application 2009/117444 A1, (2009) 109 pp.), (Zvonok et al *Chem. Biol.* (2008) 15: 854-862), (Zvonok et al *J. Proteome Res.* (2008) 7: 158-2164).

Example 79. Preparation of Transmembrane Domain-Deleted Rat FAAH (ΔTM rFAAH)

Rat ΔTM FAAH was expressed in *E. coli* cells and purified using the procedure disclosed by Patricelli et al. *Biochemistry* (1998) 37: 15177-15187.

Example 80. Preparation of Human FAAH in Fusion with N-Terminal Maltose Binding Tag (MBP ΔTM hFAAH)

Human FAAH without putative transmembrane domain following maltose binding protein was expressed in *E. coli* cells using pMALcE4 vector Alapafuja et al *J. Med. Chem.* (2012) 55: 10074-89.

Example 81. Fluorescent Assay Protocol for Rat ΔTM FAAH

Procedure was followed as described for hMGL, except that arachidonoyl-methyl coumarin (was used as fluorigenic substrate. Compounds were diluted in 50:50 DMSO/assay buffer (50 mM HEPES, 1 mM EDTA, 0.1% BSA, pH 7.4) so as to have a final DMSO concentration below 8% in each reaction. For the screening assay, 3 concentrations (1 μM, 10 μM, and 100 μM) of test compounds, 15 jag of ΔTM rFAAH and assay buffer were pre-incubated for 15 min at 25° C. AAMCA (20 μM, 2×Km) was added prior to incubation at 25° C. and kinetic fluorescence reading every 20 minutes ($\lambda_{ex}=360/\lambda_{em}=460$) for 4 hours on a BioTek Synergy HT Microplate Reader (BioTek Instruments, Winooski, Vt.). The fluorescence reading at the 3 hour time point (linear enzyme kinetics) was used to calculate percent inhibition based on control assays without inhibitor present. All FAAH assays were performed in triplicate for each inhibitor concentration, and IC$_{50}$ values determined using Prizm software (GraphPad Software, Inc.).

Example 82. Fluorescent Assay Protocol for hFAAH

Procedure was followed as described for rFAAH.

Example 83. Fluorescent Assays Protocol for hABHD6

Initial Fluorescent Inhibition Assay (3-Point)—
In each well of a 96-well plate 8 μL of membrane fraction containing full-length hABHD6 (1 μg total protein) was mixed with 168 μL of assay buffer (50 mM Tris-HCl, pH 7.6), and 20 μL of diluted compound (diluted in a dilution buffer consisting of 50% DMSO/50% assay buffer v/v). Each plate was incubated at RT for 15 minutes before adding 4 μL of 1 mM AHMMCE substrate (final concentration of 20 μM AHMMCE and final volume of 200 μL). The reaction was allowed to proceed for 1 hr at RT before the fluorescence was read at $\lambda_{ex}$ 360 nm and $\lambda_{em}$ 460 nm and the inhibition calculated. Each experiment can test 8 compounds at three concentrations (usually 10 μM, 1 μM, and 100 nM).

IC$_{50}$ Determination Assay (8-Point)—
A more detailed assay with an extended range tests compounds over 8 concentrations depending on the predetermined approximate IC50 value from the initial screen. The eight concentrations are chosen such that the lowest concentrations do not inhibit the enzyme at all and the highest concentrations inhibit the enzyme to within 10% of the 100% relative positive control. The assay was conducted in 96 well plate with each well containing the same reaction mixture detailed above in the 3-point screen. The relative fluorescence is quantified into coumarin produced by using a standard curve of HMMC in triplicate on each plate. Results are normalized to the negative control wells and the IC50 is determined using a non-linear regression curve fit in Prism, version 5 (GraphPad, San Diego, Calif.).

Biological Data
For Table 1 the ABHD6, MGL, FAAH inhibition as IC$_{50}$ μM index is as follows:
A=0.01 μM-0.1 μM
B=>0.1 μM-1.00 μM
C=>1.00 μM

TABLE 1

| Example No. | ABHD6 Inhibition IC$_{50}$ μM | hMGL Inhibition IC$_{50}$ μM | rFAAH Inhibition IC$_{50}$ μM | hFAAH Inhibition IC$_{50}$ μM |
|---|---|---|---|---|
| 1 | A | C | C | C |
| 2 | C | C | C | C |
| 3 | C | C | C | C |
| 4 | A | C | C | C |
| 5 | C | C | C | NT |
| 6 | C | C | C | C |
| 7 | C | C | C | C |
| 8 | A | C | C | C |
| 9 | A | C | C | C |
| 10 | B | C | C | C |
| 11 | B | C | C | C |
| 12 | B | C | C | C |
| 13 | C | C | C | C |
| 14 | B | C | C | C |
| 15 | C | C | C | C |
| 16 | A | C | C | C |
| 17 | A | C | C | C |
| 18 | B | C | C | C |
| 19 | A | C | C | C |
| 20 | B | C | C | C |
| 21 | A | C | C | C |
| 22 | A | C | C | NT |
| 23 | A | C | C | NT |
| 24 | C | C | C | C |
| 25 | A | C | C | NT |
| 26 | A | C | C | C |
| 27 | C | C | C | C |
| 28 | B | C | C | NT |
| 29 | B | C | C | NT |
| 30 | A | C | C | NT |
| 31 | A | C | C | NT |
| 32 | A | C | C | NT |
| 35 | A | C | C | NT |
| 37 | B | C | C | NT |
| 38 | C | C | C | NT |
| 39 | A | C | C | NT |
| 40 | A | C | C | NT |

TABLE 1-continued

| Example No. | ABHD6 Inhibition IC$_{50}$ μM | hMGL Inhibition IC$_{50}$ μM | rFAAH Inhibition IC$_{50}$ μM | hFAAH Inhibition IC$_{50}$ μM |
|---|---|---|---|---|
| 41 | A | C | C | NT |
| 42 | A | C | C | NT |
| 43 | A | C | C | NT |
| 44 | B | C | C | NT |
| 45 | A | A | C | C |
| 46 | A | A | C | NT |
| 47 | A | C | C | NT |
| 48 | A | A | C | NT |
| 49 | A | A | C | NT |
| 50 | A | A | C | NT |
| 52 | A | A | C | C |
| 53 | A | A | C | C |
| 54 | A | NT | NT | NT |
| 55 | A | NT | NT | NT |
| 56 | A | B | NT | NT |
| 57 | A | B | NT | NT |
| 58 | A | NT | NT | NT |
| 59 | A | A | A | NT |
| 60 | A | C | C | C |
| 61 | A | NT | NT | NT |
| 63 | A | C | C | C |
| 64 | A | C | C | C |
| 67 | A | A | A | C |
| 68 | C | A | A | C |

NT = Not tested

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A compound of formula II:

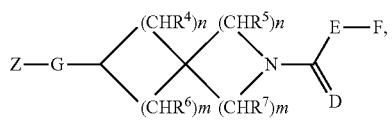

Formula II or a stereoisomer thereof, or a pharmaceutically acceptable salt of either of the foregoing,
wherein:
D=O or S;
E=O, NH, or none, when E is none, F is directly attached to C=D;
F is selected from

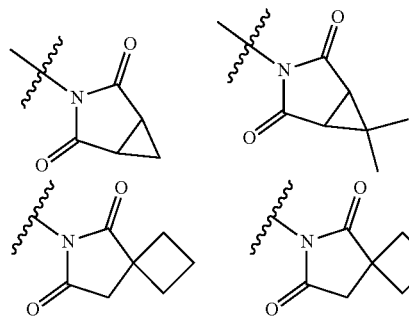

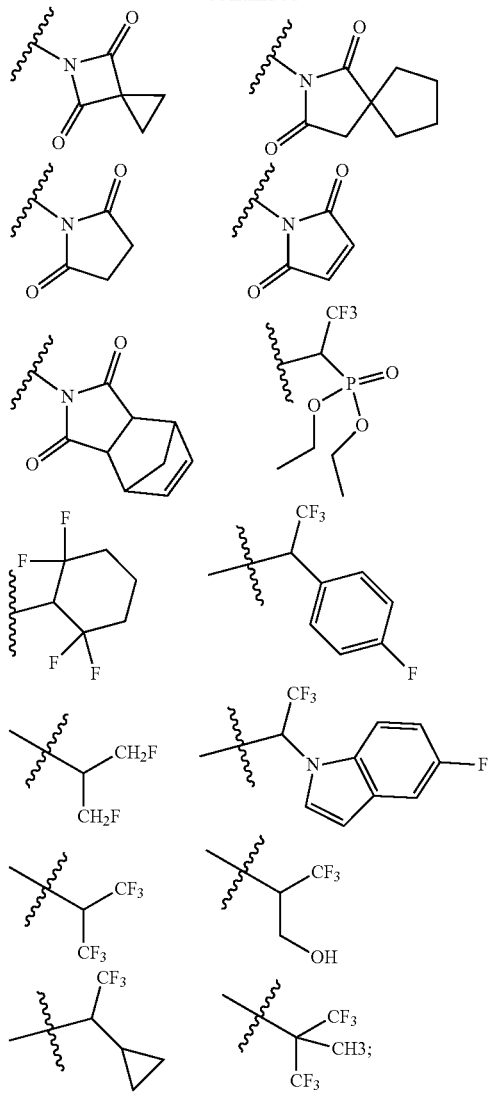

each n is 1, and each m is independently 1 or 2;
G=O, NH, NR$^{13}$, or none, when G is none, G is directly attached to the cyclic ring;
Z is selected from H; halogen; C$_1$-C$_{10}$alkyl; C$_1$-C$_{10}$alkyl-oxy; C$_3$-C$_8$cycloalkyl; C$_3$-C$_8$cycloalkyl-oxy; C$_1$-C$_{10}$alkyl or C$_1$-C$_{10}$alkyl-oxy substituted at the terminal carbon with halogen, haloalkyl, haloalkoxy, alkoxy, alkenyl, alkynyl, NR$^8$R$^9$, CN, ONO$_2$, aryl, O-aryl, O-aralkyl, NR$^{10}$-aryl, NR$^{11}$-aralkyl, O-heteroaryl, NR$^{12}$-heteroaryl, or saturated or unsaturated four-, five-, six- or seven-membered ring which can contain up to 3 heteroatoms selected from N, N-oxide, S and O; or saturated or unsaturated four-, five-, six- or seven-membered ring which can contain up to 3 heteroatoms selected from N, N-oxide, S and O;
R$^4$, R$^5$, R$^6$, and R$^7$ are each independently H or C$_1$-C$_3$ alkyl; and
R$^8$, R$^9$, R$^{10}$, R$^{11}$, R$^{12}$, and R$^{13}$ are each independently H, C$_1$-C$_5$alkyl, or C$_3$-C$_8$cycloalkyl.

2. The compound according to claim 1, wherein E=O or NH.

3. The compound according to claim 2, wherein E=O.

4. The compound according to claim 1, selected from the group consisting of:

1,1,1,3,3,3-Hexafluoropropan-2-yl 6-(3-(trifluoromethyl)phenoxy)-2-azaspiro [3.3] heptane-2-carboxylate;

1,1,1,3,3,3-Hexafluoropropan-2-yl-6-(3-fluorophenoxy)-2-azaspiro[3.3]heptane-2-carboxylate;

1,1,1,3,3,3-Hexafluoropropan-2-yl-6-(3-methoxyphenoxy)-2-azaspiro[3.3]heptane-2-carboxylate;

1,1,1,3,3,3-Hexafluoropropan-2-yl-6-(3-phenoxyphenoxy)-2-azaspiro[3.3]heptane-2-carboxylate;

1,1,1,3,3,3-Hexafluoropropan-2-yl 6-(3-(trifluoromethoxy)phenoxy)-2-azaspiro[3.3] heptane-2-carboxylate;

1,1,1,3,3,3-Hexafluoropropan-2-yl 2-(3-fluorophenoxy)-6-azaspiro[3.4]octane-6-carboxylate;

1,1,1,3,3,3-Hexafluoropropan-2-yl 2-(3-fluorophenoxy)-6-azaspiro[3.4]octane-6-carboxylate;

1,1,1,3,3,3-Hexafluoropropan-2-yl 6-(3-fluorophenoxy)-2-azaspiro[3.4]octane-2-carboxylate;

1,1,1,3,3,3-Hexafluoropropan-2-yl 6-((5-fluoropyridin-3-yl)oxy)-2-azaspiro[3.3]heptane-2-carboxylate;

1,1,1,3,3,3-Hexafluoropropan-2-yl 6-(5-fluoropyridin-3-yl)oxy)-2-azaspiro[3.4]octane-2-carboxylate;

1,1,1,3,3,3-Hexafluoropropan-2-yl 6-(benzo[d]isoxazol-6-yloxy)-2-azaspiro[3.3]heptane-2-carboxylate;

6,6-Dimethyl-2,4-dioxo-3-azabicyclo[3.1.0]hexan-3-yl 6-(3-(trifluoromethyl)phenoxy)-2-azaspiro[3.3]heptane-2-carboxylate;

6,6-Dimethyl-2,4-dioxo-3-azabicyclo[3.1.0]hexan-3-yl 6-(5-fluoropyridin-3-yl)oxy)-2-azaspiro[3.4]octane-2-carboxylate;

1,1,1,3,3,3-Hexafluoropropan-2-yl 6-((3-(trifluoromethyl)phenyl)amino)-2-azaspiro[3.3]heptane-2-carboxylate;

1,1,1,3,3,3-hexafluoropropan-2-yl 6-((3-methoxyphenyl)amino)-2-azaspiro[3.3]heptane-2-carboxylate;

1,1,1,3,3,3-Hexafluoropropan-2-yl (2r,4s)-2-(bis(4-fluorophenyl)methoxy)-6-azaspiro[3.4]octane-6-carboxylate;

1,1,1,3,3,3-Hexafluoropropan-2-yl (2s,4r)-2-(bis(4-fluorophenyl)methoxy)-6-azaspiro[3.4]octane-6-carboxylate;

1,1,1,3,3,3-hexafluoropropan-2-yl 6-(bis(4-fluorophenyl)methoxy)-2-azaspiro[3.4]octane-2-carboxylate;

1,1,1,3,3,3-Hexafluoropropan-2-yl 6-(bis(4-fluorophenyl)methoxy)-2-azaspiro[3.3]heptane-2-carboxylate;

1,1,1,3,3,3-Hexafluoropropan-2-yl 2-(benzyloxy)-6-azaspiro[3.4]octane-6-carboxylate;

1,1,1,3,3,3-hexafluoropropan-2-yl (2s,4r)-2-((bis(4-fluorophenyl)methyl)amino)-6-azaspiro[3.4]octane-6-carboxylate;

1,1,1,3,3,3-hexafluoropropan-2-yl 6-((5-methoxypyridin-3-yl)amino)-2-azaspiro[3.3]heptane-2-carboxylate; and 1,1,1,3,3,3-hexafluoropropan-2-yl 6-(5-fluoropyridin-3-yl)amino)-2-azaspiro[3.3]heptane-2-carboxylate, or a stereoisomer thereof, or a pharmaceutically acceptable salt of either of the foregoing.

5. A method of treating a cannabinoid receptor-mediated disease or disorder in a patient in need thereof, comprising administering to the patient a therapeutically effective amount of a compound of claim 1, or a stereoisomer thereof, or a pharmaceutically acceptable salt of either of the foregoing.

6. The method of claim 5, wherein the disease or disorder is Type-2 diabetes, ocular disease, pain, neuropathic pain, a neurodegenerative disease, spinal cord injury, a mental disorder, a gastrointestinal motility disorder, a coronary artery disease, ocular hypertension, or an eating disorder.

7. A pharmaceutical composition comprising a pharmaceutically acceptable carrier and a compound of claim 1, or a stereoisomer thereof, or a pharmaceutically acceptable salt of either of the foregoing.

8. The composition according to claim 7, wherein the compound is selected from the group consisting of:

1,1,1,3,3,3-Hexafluoropropan-2-yl 6-(3-(trifluoromethyl)phenoxy)-2-azaspiro [3.3] heptane-2-carboxylate;

1,1,1,3,3,3-Hexafluoropropan-2-yl-6-(3-fluorophenoxy)-2-azaspiro[3.3]heptane-2-carboxylate;

1,1,1,3,3,3-Hexafluoropropan-2-yl-6-(3-methoxyphenoxy)-2-azaspiro[3.3]heptane-2-carboxylate;

1,1,1,3,3,3-Hexafluoropropan-2-yl-6-(3-phenoxyphenoxy)-2-azaspiro[3.3]heptane-2-carboxylate;

1,1,1,3,3,3-Hexafluoropropan-2-yl 6-(3-(trifluoromethoxy)phenoxy)-2-azaspiro[3.3] heptane-2-carboxylate;

1,1,1,3,3,3-Hexafluoropropan-2-yl 2-(3-fluorophenoxy)-6-azaspiro[3.4]octane-6-carboxylate;

1,1,1,3,3,3-Hexafluoropropan-2-yl 2-(3-fluorophenoxy)-6-azaspiro[3.4]octane-6-carboxylate;

1,1,1,3,3,3-Hexafluoropropan-2-yl 6-(3-fluorophenoxy)-2-azaspiro[3.4]octane-2-carboxylate;

1,1,1,3,3,3-Hexafluoropropan-2-yl 6-((5-fluoropyridin-3-yl)oxy)-2-azaspiro[3.3]heptane-2-carboxylate;

1,1,1,3,3,3-Hexafluoropropan-2-yl 6-(5-fluoropyridin-3-yl)oxy)-2-azaspiro[3.4]octane-2-carboxylate;

1,1,1,3,3,3-Hexafluoropropan-2-yl 6-(benzo[d]isoxazol-6-yloxy)-2-azaspiro[3.3]heptane-2-carboxylate;

6,6-Dimethyl-2,4-dioxo-3-azabicyclo[3.1.0]hexan-3-yl 6-(3-(trifluoromethyl)phenoxy)-2-azaspiro[3.3]heptane-2-carboxylate;

6,6-Dimethyl-2,4-dioxo-3-azabicyclo[3.1.0]hexan-3-yl 6-(5-fluoropyridin-3-yl)oxy)-2-azaspiro[3.4]octane-2-carboxylate;

1,1,1,3,3,3-Hexafluoropropan-2-yl 6-((3-(trifluoromethyl)phenyl)amino)-2-azaspiro[3.3]heptane-2-carboxylate;

1,1,1,3,3,3-hexafluoropropan-2-yl 6-((3-methoxyphenyl)amino)-2-azaspiro[3.3]heptane-2-carboxylate;

1,1,1,3,3,3-Hexafluoropropan-2-yl (2r,4s)-2-(bis(4-fluorophenyl)methoxy)-6-azaspiro[3.4]octane-6-carboxylate;

1,1,1,3,3,3-Hexafluoropropan-2-yl (2s,4r)-2-(bis(4-fluorophenyl)methoxy)-6-azaspiro[3.4]octane-6-carboxylate;

1,1,1,3,3,3-hexafluoropropan-2-yl 6-(bis(4-fluorophenyl)methoxy)-2-azaspiro[3.4]octane-2-carboxylate;

1,1,1,3,3,3-Hexafluoropropan-2-yl 6-(bis(4-fluorophenyl)methoxy)-2-azaspiro[3.3]heptane-2-carboxylate;

1,1,1,3,3,3-Hexafluoropropan-2-yl 2-(benzyloxy)-6-azaspiro[3.4]octane-6-carboxylate;

1,1,1,3,3,3-hexafluoropropan-2-yl (2s,4r)-2-((bis(4-fluorophenyl)methyl)amino)-6-azaspiro[3.4]octane-6-carboxylate;

1,1,1,3,3,3-hexafluoropropan-2-yl 6-((5-methoxypyridin-3-yl)amino)-2-azaspiro[3.3]heptane-2-carboxylate; and 1,1,1,3,3,3-hexafluoropropan-2-yl 6-((5-fluoropyridin-3-yl)amino)-2-azaspiro[3.3]heptane-2-carboxylate, or a stereoisomer thereof, or a pharmaceutically acceptable salt of either of the foregoing.

* * * * *